US012655148B2

(12) United States Patent
Xu et al.

(10) Patent No.: US 12,655,148 B2
(45) Date of Patent: *Jun. 16, 2026

(54) FXR SMALL-MOLECULE AGONIST, AND PREPARATION METHOD THEREFOR AND USE THEREOF

(71) Applicant: Shanghai Institute of Materia Medica, Chinese Academy of Sciences, Pudong Shanghai (CN)

(72) Inventors: Huaqiang Xu, Pudong Shanghai (CN); Jia Li, Pudong Shanghai (CN); Jingjing Shi, Pudong Shanghai (CN); Yi Zang, Pudong Shanghai (CN); Dandan Sun, Pudong Shanghai (CN); Mingliang Liu, Pudong Shanghai (CN); Rongrong Xie, Pudong Shanghai (CN); Erli You, Pudong Shanghai (CN); Lixin Gao, Pudong Shanghai (CN); Qian Tan, Pudong Shanghai (CN)

(73) Assignee: SHANGHAI INSTITUTE OF MATERIA MEDICA, CHINESE ACADEMY OF SCIENCES, Shanghai (CN)

( * ) Notice: Subject to any disclaimer, the term of this patent is extended or adjusted under 35 U.S.C. 154(b) by 576 days.

This patent is subject to a terminal disclaimer.

(21) Appl. No.: 18/029,359

(22) PCT Filed: Sep. 28, 2021

(86) PCT No.: PCT/CN2021/121313

§ 371 (c)(1),
(2) Date: Mar. 29, 2023

(87) PCT Pub. No.: WO2022/068815

PCT Pub. Date: Apr. 7, 2022

(65) Prior Publication Data

US 2023/0357244 A1 Nov. 9, 2023

(30) Foreign Application Priority Data

Sep. 30, 2020 (CN) ........................ 202011061216.0

(51) Int. Cl.
*C07D 413/14* (2006.01)
*A61K 31/46* (2006.01)
*C07D 471/08* (2006.01)

(52) U.S. Cl.
CPC ................................ *C07D 471/08* (2013.01)

(58) Field of Classification Search
CPC .... C07D 413/14; C07D 451/02; A61K 31/46; A61P 1/16; A61P 3/00; A61P 3/10; A61P 29/00
USPC .......................................... 546/125; 514/304
See application file for complete search history.

(56) References Cited

U.S. PATENT DOCUMENTS

| | | | | |
|---|---|---|---|---|
| 9,150,568 | B2 | 10/2015 | Tully et al. | |
| 9,751,874 | B2 | 9/2017 | Gege et al. | |
| 11,667,629 | B2 | 6/2023 | Liu et al. | |
| 12,240,841 | B2 * | 3/2025 | Xu | A61P 3/00 |
| 2015/0366856 | A1 | 12/2015 | Tully et al. | |
| 2022/0213083 | A1 | 7/2022 | Xu et al. | |

FOREIGN PATENT DOCUMENTS

| | | | |
|---|---|---|---|
| CN | 107973790 | A | 5/2018 |
| CN | 108017636 | A | 5/2018 |
| CN | 108064223 | A | 5/2018 |
| CN | 108602811 | A | 9/2018 |
| CN | 109265471 | A | 1/2019 |
| CN | 109906223 | A | 6/2019 |
| CN | 111825667 | A | 10/2020 |
| CN | 112812114 | A | 5/2021 |
| JP | 2014-500317 | A | 1/2014 |
| JP | 2018-500304 | A | 1/2018 |

(Continued)

OTHER PUBLICATIONS

Extended European Search Report issued Sep. 23, 2024 in EP Application No. 21874475.3.
Office Action issued Aug. 12, 2024 in U.S. Appl. No. 17/603,823, by Xu.
STNext Accession No. 1997:727377 to Kaminsky (1997).
International Search Report and Written Opinion issued Mar. 31, 2023 in SG Application No. 11202111502X.
Ballatore et al., "Carboxylic Acid (Bio)Isosteres in Drug Design," ChemMedChem, vol. 8(3), pp. 385-395 (2013).
Meanwell, N., "Synopsis of Some Recent Tactical Application of Bioisosteres in Drug Design," Journal of Medicinal Chemistry, vol. 54, pp. 2529-2591 (2011).

(Continued)

*Primary Examiner* — Charanjit Aulakh
(74) *Attorney, Agent, or Firm* — Panitch Schwarze Belisario & Nadel LLP

(57) ABSTRACT

A strong FXR small-molecule agonist, and a preparation method therefor and use thereof, the structure of the agonist being represented by formula (I), are provided. In the formula, each substituent is as defined in the description and the claims. The compound provided has the advantages of high FXR agonist activity, simple synthesis, easily available raw materials and the like, and can be used for preparing medicines for treating FXR related diseases.

(I)

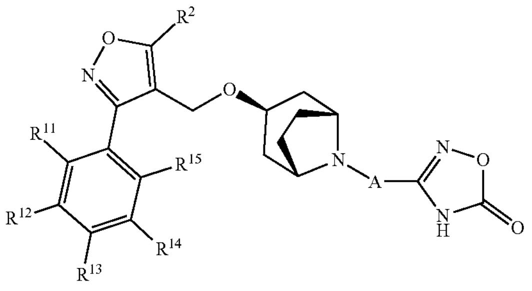

13 Claims, No Drawings

(56) References Cited

FOREIGN PATENT DOCUMENTS

| | | | |
|---|---|---|---|
| JP | 7398605 | B2 | 12/2023 |
| WO | 2009012125 | A1 | 1/2009 |
| WO | 2012087519 | A1 | 6/2012 |
| WO | 2017133521 | A1 | 8/2017 |
| WO | 2018039386 | A1 | 3/2018 |
| WO | 2018085148 | A1 | 5/2018 |
| WO | 2019007418 | A1 | 1/2019 |
| WO | 2020011146 | A1 | 1/2020 |
| WO | 2020114307 | A1 | 6/2020 |
| WO | 2020156241 | A1 | 8/2020 |
| WO | 2020211872 | A1 | 10/2020 |

OTHER PUBLICATIONS

Office Action issued Mar. 11, 2024 in JP Application No. 2023-519904.

Notice of Allowance issued Oct. 30, 2024 in U.S. Appl. No. 17/603,823, by Xu.

Int'l Search Report and Written Opinion mailed Jul. 8, 2020 in Int'l Application No. PCT/CN2020/085713.

Office Action issued Apr. 19, 2022 in Indian Application No. 202137052539.

European Extended Search Report issued on Nov. 15, 2022 in EP Application 20791301.3.

International Search Report issued Jan. 7, 2020 in PCT/CN2021/121313.

* cited by examiner

FXR SMALL-MOLECULE AGONIST, AND PREPARATION METHOD THEREFOR AND USE THEREOF

CROSS-REFERENCE TO RELATED APPLICATIONS

This application is a Section 371 of International Application No. PCT/CN2021/121313, filed Sep. 28, 2021, which was published in the Chinese language on Apr. 7, 2022 under International Publication No. WO 2022/068815 A1, which claims priority under 35 U.S.C. § 119 (b) to Chinese Application No. 202011061216.0, filed Sep. 30, 2020, the disclosures of which are incorporated herein by reference in their entireties.

TECHNICAL FIELD

The present invention relates to the field of medicine, and relates to a class of compounds as FXR agonist and preparation therefor and use thereof. Specifically, it relates to a class of non-steroidal compounds that can be used as FXR agonist and the enantiomer, diastereomer, tautomer, solvate, prodrug, or pharmaceutically acceptable salt thereof, the preparation method therefor and use thereof in the manufacture of a medicament for the treatment of FXR-related disease.

BACKGROUND TECHNIQUE

Nuclear receptors are widely present in organisms and are a type of nuclear transcription regulators that rely on specific ligand activation. Metabolic nuclear receptors are a type of nuclear receptors that regulate substance metabolism, cell proliferation, and apoptosis in the body. Farnesoid X receptor (FXR) is a member of the nuclear receptor superfamily, which was first discovered by Foman et al. in 1995 and named because its transcriptional activity can be enhanced by farnesoid.

The FXR structure contains ligand-independent transcription activation function domain (AF1) at amino-terminal, DNA binding domain (DBD), hinge region, ligand binding domain (LBD) and ligand-dependent transcription activation function domain (AF2) at carbon-terminal, which is a typical nuclear receptor structure. FXR is activated by bile acids in the body and participates in the processes of bile acid metabolism, lipid metabolism, and sugar metabolism in the living body. The mechanism by which FXR regulates bile acid metabolism and transport is mainly accomplished by regulating the transcription of cholesterol 7α-hydroxylase (CYP7A1) which is a rate-limiting enzyme of bile acid synthesis. Although FXR cannot directly act on the CYP7A1 promoter, it can induce the expression of small heterodimer partner (SHP) and combine HNF-4α (hepatocyte nuclear factor 4α) and LRH-1 (liver receptor homolog) to down-regulate the transcription of CYP7A1. In the process of lipid metabolism, FXR in the liver regulates lipid metabolism and transport to reduce plasma free fatty acids and triglycerides by directly or indirectly regulating PPARα, VLDL receptor (very low density lipoprotein receptor, VLDLR), proprotein convertase subtilisin kexin type 9 (PCSK9), scavenger receptor group B type 1 (SRB1), phosphor lipid transfer protein (PLTP), liver X receptor (LXR), sterol regulatory element-binding protein-1C (SREBP-1C) and fatty acid synthetase (FAS), and activating lipoprotein lipase (LPL) and the like. In the process of glucose metabolism, the activation of FXR can promote liver glycogen synthesis and increase insulin sensitivity and insulin secretion to control blood glucose levels in the body. Since FXR plays an important role in the processes of bile acid metabolism, lipid metabolism and glucose metabolism, FXR ligand small molecule compounds are expected to be used as new medicament for the treatment of hypertriglyceridemia, type 2 diabetes, metabolic syndrome, NAFLD and other metabolic-related diseases.

SUMMARY OF THE INVENTION

The object of the present invention is to provide a FXR small molecule agonist and preparation method therefor and use thereof.

In the first aspect of the present invention, it provides a compound represented by general formula I, or a tautomer, solvate, prodrug or pharmaceutically acceptable salt thereof, (I)

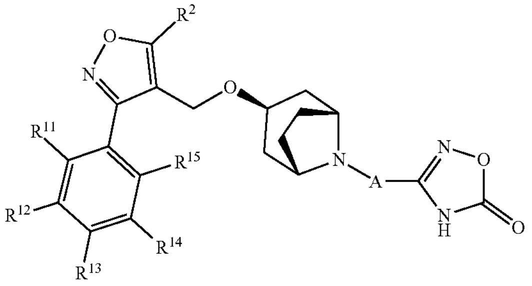

wherein $R^{11}$, $R^{12}$, $R^{13}$, $R^{14}$ and $R^{15}$ are each independently hydrogen, halogen, halogenated $C_{1-6}$ alkyl, halogenated $C_1$-$C_6$ alkoxy, $C_1$-$C_6$ alkyl, $C_{1-6}$ alkoxy, $C_3$-$C_6$ cycloalkyl, $C_3$-$C_6$ cycloalkoxy, cyano or nitro;

$R^2$ is $C_6$-$C_{12}$ aryl, $C_1$-$C_6$ alkyl or $C_3$-$C_6$ cycloalkyl;

A is the following substituted or unsubstituted group: phenyl, pyridyl, thienyl, furyl, indazolyl, indolyl, benzothienyl, benzofuranyl, and the "substituted" means that there is one, two or three substituents selected from the group consisting of halogen, $C_1$-$C_6$ alkyl, halogenated $C_{1-6}$ alkyl, halogenated $C_1$-$C_6$ alkoxy, $C_3$-$C_6$ cycloalkyl, $C_1$-$C_6$ alkoxy, and $C_3$-$C_6$ cycloalkoxy.

In another preferred example, $R^{11}$, $R^{12}$, $R^{13}$, $R^{14}$ and $R^{15}$ are each independently hydrogen, fluorine, chlorine, bromine, methyl, ethyl, n-propyl, isopropyl, n-butyl, isobutyl, trifluoromethyl, or trifluoromethoxy.

In another preferred example, $R^{12}$, $R^{13}$ and $R^{14}$ are hydrogen.

In another preferred example, $R^{11}$ and $R^{15}$ are each independently hydrogen, chlorine, bromine, trifluoromethyl, or trifluoromethoxy.

In another preferred example, $R^2$ is phenyl, methyl, ethyl, n-propyl, isopropyl, n-butyl, isobutyl, cyclopropyl, cyclobutyl or cyclopentyl.

In another preferred example, A is the following substituted or unsubstituted group: phenyl, pyridyl; and the "substituted" means that there is one or two substituents selected from the group consisting of fluorine, chlorine, bromine, $C_1$-$C_4$ alkyl, $C_3$-$C_6$ cycloalkyl, $C_1$-$C_4$ alkoxy, and $C_3$-$C_6$ cycloalkoxy.

In another preferred example, A is the following substituted or unsubstituted group: phenyl, pyridyl; A is the following substituted or unsubstituted group: phenyl, pyridyl, indolyl; and the "substituted" means that there is one or two substituents selected from the group consisting of fluorine, chlorine, bromine, trifluoromethyl, trifluoromethoxy, methyl, ethyl, propyl.

In the present invention, when there are two or more substituents, each substituent is the same or different.

In another preferred example, A is phenyl,

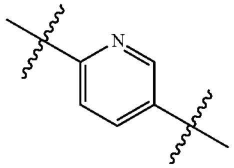

or

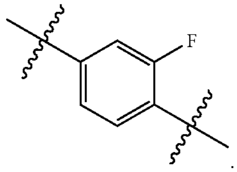

In another preferred example, the pharmaceutically acceptable salt in the present invention refers to a salt formed from inorganic acid such as phosphoric acid, sulfuric acid, hydrochloric acid, etc., or a salt from organic acid such as acetic acid, tartaric acid, citric acid, malic acid, etc., or from acidic amino acid such as aspartic acid, glutamic acid, etc.; or a salt formed from inorganic base, such as sodium, potassium, calcium, aluminum and ammonium salts.

In another preferred example, the compound is:

1

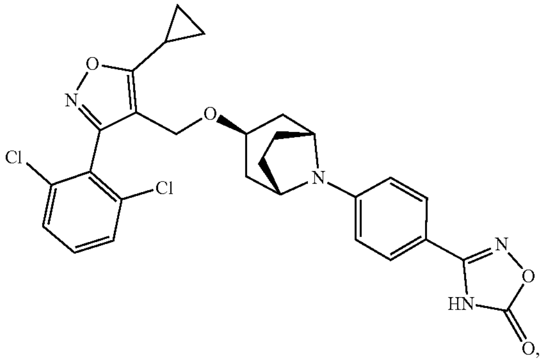

3

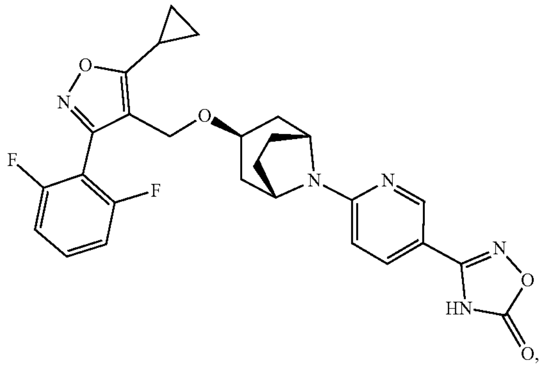

-continued

4

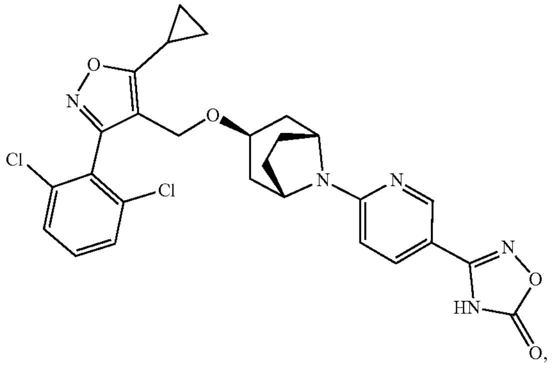

5

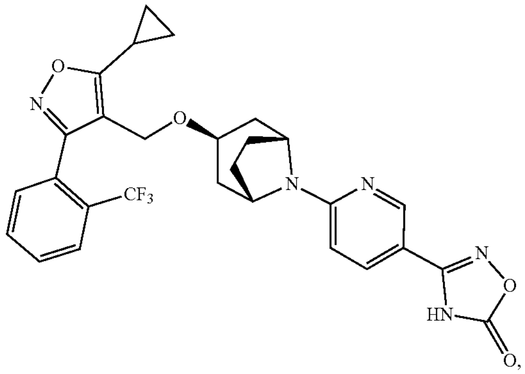

6

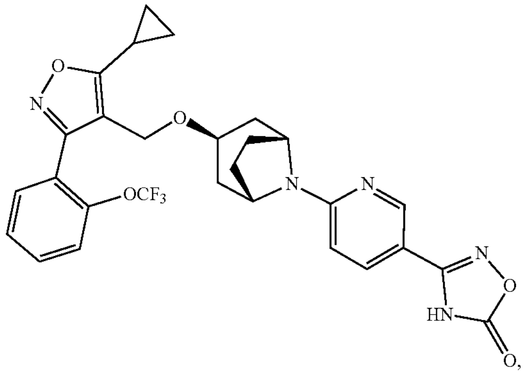

7

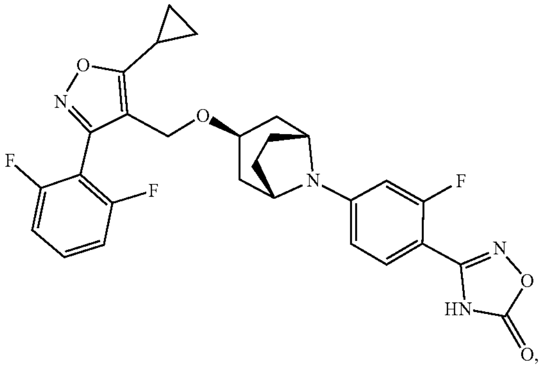

-continued
8
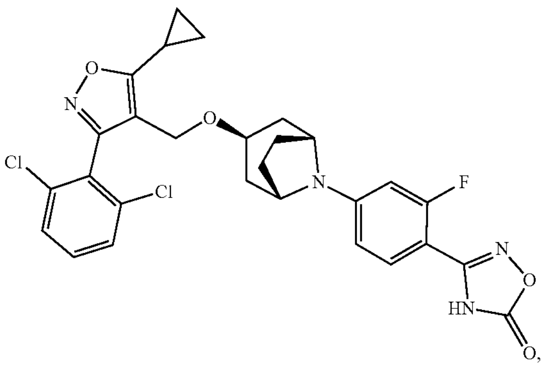
,
9
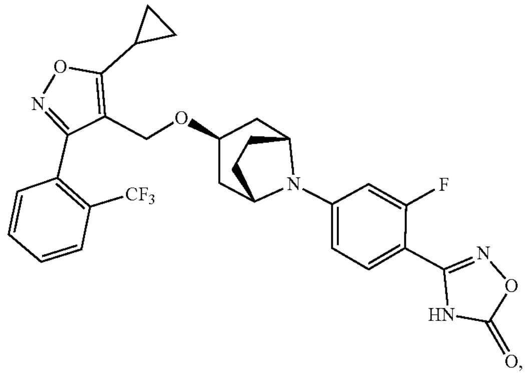
,
10
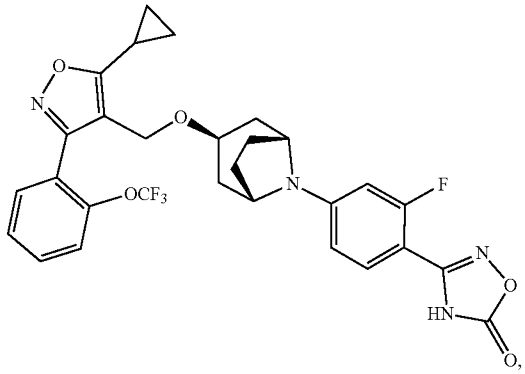
,
11
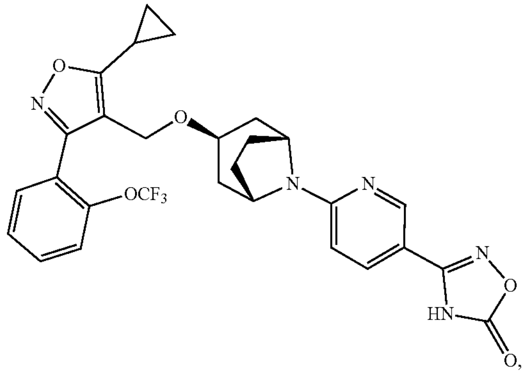
,
-continued
12
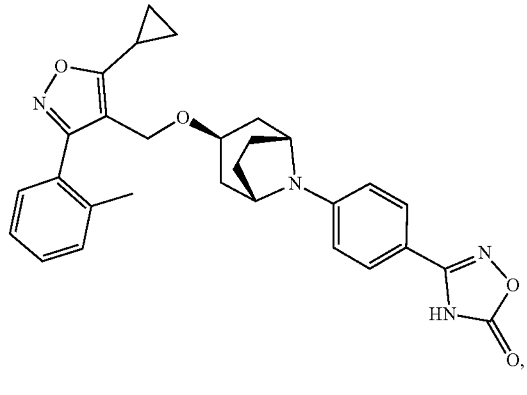
,
13
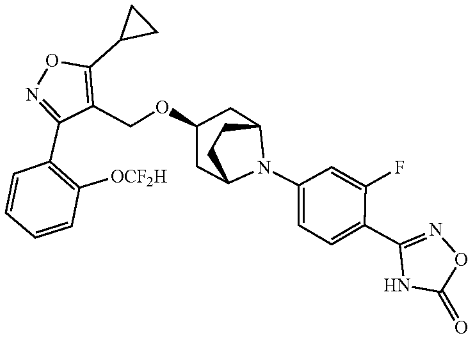
or
14
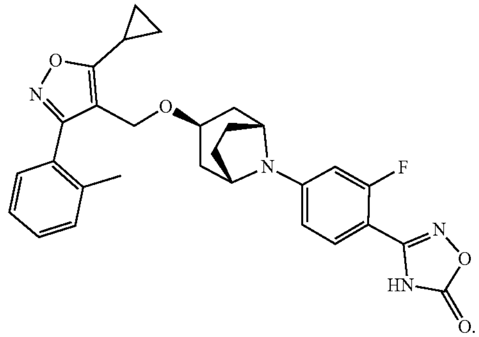
.
In the second aspect of the present invention, it provides a method for preparing the compound according to the first aspect, which includes the following steps:
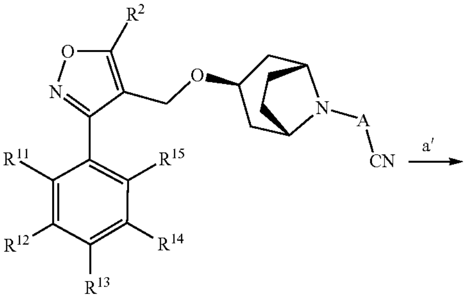
VII -continued

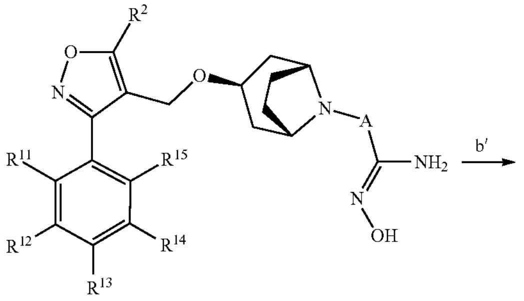

VIII

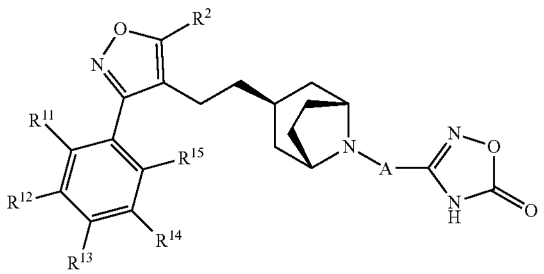

I (a') reacting a compound represented by general formula VII with hydroxylamine hydrochloride to produce a compound represented by general formula VIII;

(b') reacting the compound represented by the general formula VIII under the action of phosgene, triphosgene, carbonyl diimidazole or thiocarbonyldiimidazole to produce the compound represented by the general formula I, wherein the definitions of $R^2$, A, $R^{11}$, $R^{12}$, $R^{13}$, $R^{14}$ and $R^{15}$ are described as above.

In another preferred example, the compound represented by general formula VII is prepared by the following steps:

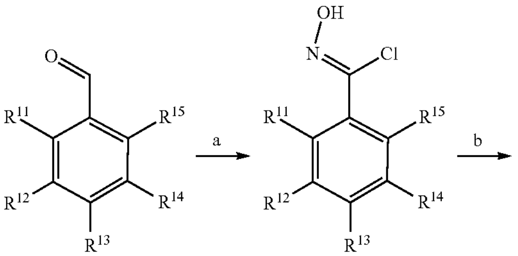

II III

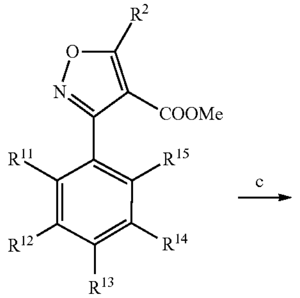

IV

-continued

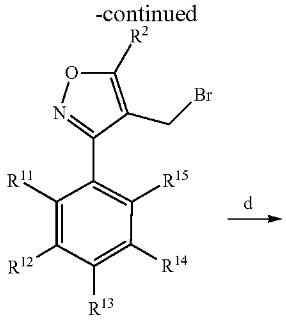

V

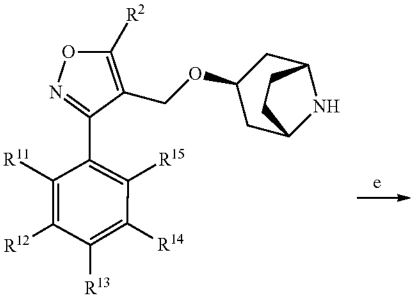

VI

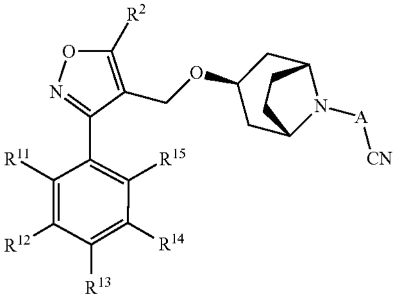

VII a) reacting substituted benzaldehyde compound represented by general formula II as starting materials with hydroxylamine hydrochloride to obtain an intermediate and then chlorinating the intermediate with N-chlorosuccinimide (NCS) to produce a compound represented by general formula III;

b) reacting the compound represented by the general formula III with 3-oxopropionate to obtain a compound represented by the general formula IV;

c) reducing the ester in the compound represented by formula IV to produce alcohol, and then brominating to produce a compound represented by V;

d) reacting the compound represented by general formula V with endo-8-azabicyclio[3.2.1]octan-3-ol to produce a compound represented by general formula VI;

e) coupling the compound represented by general formula VI with Br-A-CN under the catalysis of copper or palladium to obtain the compound represented by general formula VII, and, in each formula, the definitions of $R^2$, A, $R^{11}$, $R^{12}$, $R^{13}$, $R^{14}$ and $R^{15}$ are described as above.

In another preferred example, the compound represented by general formula VII is prepared by the following steps:

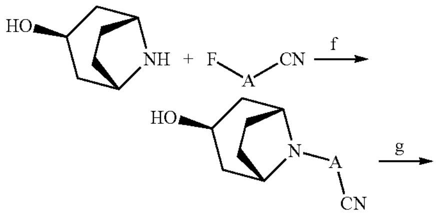

IX

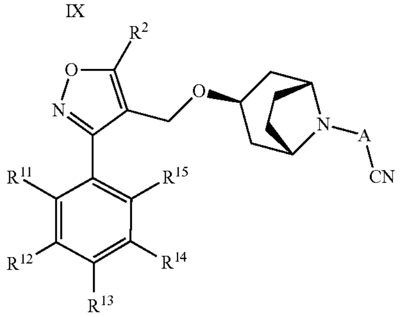

VII f) reacting endo-8-azabicyclio[3.2.1]octan-3-ol with F-A-CN to generate a compound represented by general formula IX;

g) reacting a compound represented by the general formula V with the compound represented by the general formula IX to produce the compound represented by the general formula VII, and, in each formula, $R^2$, A, $R^1$, $R^{12}$, $R^{13}$, $R^{14}$ and $R^{15}$ are defined as above.

In the third aspect of the present invention, it provides a pharmaceutical composition, comprising:

the compound represented by the general formula I according to the first aspect, or the tautomer, solvate, prodrug, or pharmaceutically acceptable salt thereof; and a pharmaceutically acceptable carrier.

The compound provided by the present invention can be used alone or mixed with pharmaceutically acceptable auxiliary material (such as excipient, diluent, etc.) to prepare tablet, capsule, granule or syrup for oral administration. The pharmaceutical composition can be prepared according to conventional methods in pharmacy.

In the fourth aspect of the present invention, it provides use of the compound represented by the general formula I according to the first aspect, or the tautomer, solvate, prodrug, or pharmaceutically acceptable salt thereof, (a) as an FXR agonist; or (b) for the manufacture of a medicament for the treatment of FXR-related disease.

In another preferred example, the FXR-related disease is a disease related to bile acid metabolism, carbohydrate metabolism, lipid metabolism, inflammation, and/or liver fibrosis.

In another preferred example, the FXR-related disease is non-alcoholic fatty liver (NASH), primary biliary cirrhosis (PBC), primary sclerosing cholangitis (PSC), gallstone, non-alcoholic liver cirrhosis, liver fibrosis, cholestatic liver disease, hyperlipidemia, hypercholesterolemia, or diabetes.

It should be understood that, within the scope of the present invention, each of the above technical features of the present invention and each of the technical features specifically described below (e.g., examples) can be combined with each other, thereby forming a new or preferred technical solution. Each feature disclosed in the specification can be replaced by any alternative feature that provides the same, equal or similar purpose. Due to space limitations, they will not be redundantly described herein.

MODES FOR CARRYING OUT THE INVENTION

After extensive and intensive researches, the inventors of the present application developed a class of non-steroidal compounds that can be used as FXR agonist, which have the ability to agitate FXR at the molecular and cellular levels. The compound of the present invention has the advantages of high FXR agonistic activity, simple synthesis, easy availability of raw materials, etc., and can be used for the manufacture of a medicament for treating FXR-related diseases. On this basis, the present invention has been completed.

Terms

In the present invention, the halogen is F, Cl, Br or I.

In the present invention, unless otherwise specified, the terms used have the general meanings known to those skilled in the art.

In the present invention, the term "$C_1$-$C_6$" refers to 1, 2, 3, 4, 5 or 6 carbon atoms, and "$C_1$-$C_8$" refers to 1, 2, 3, 4, 5, 6, 7 or 8 carbon atoms, and so on. "3-10 membered" refers to 3-10 ring atoms, and so on.

In the present invention, the term "alkyl" refers to a saturated linear or branched hydrocarbon moiety. For example, the term "$C_1$-$C_6$ alkyl" refers to a straight or branched chain alkyl having 1 to 6 carbon atoms, including but not limited to methyl, ethyl, n-propyl, isopropyl, n-butyl, isobutyl, sec-butyl, tert-butyl, pentyl and hexyl, etc.; preferably ethyl, n-propyl, isopropyl, n-butyl, isobutyl, sec-butyl and tert-butyl.

In the present invention, the term "alkoxy" means —O—($C_1$-$C_6$ alkyl) group. For example, the term "$C_1$-$C_6$ alkoxy" refers to a straight or branched chain alkoxy having 1 to 6 carbon atoms, including but not limited to methoxy, ethoxy, n-propoxy, isopropoxy, butoxy and so on.

In the present invention, the term "cycloalkyl" refers to a saturated cyclic hydrocarbon moiety, for example, the term "$C_3$-$C_{10}$ cycloalkyl" refers to a cyclic alkyl group having 3 to 10 carbon atoms in the ring, including but not limited to cyclopropyl, cyclobutyl, cyclopentyl, cyclohexyl, cycloheptyl, cyclooctyl, cyclodecyl and the like. The terms "$C_3$-$C_8$ cycloalkyl", "$C_3$-$C_7$ cycloalkyl" and "$C_3$-$C_6$ cycloalkyl" have similar meanings.

In the present invention, the term "cycloalkoxy" means cycloalkyl-O—, and cycloalkyl is described as above.

In the present invention, the term "4-7 membered nitrogen-containing heterocyclyl" refers to a cycloalkyl ring having 3-7 ring atoms and containing 1, 2 or 3 N atoms, and includes, but not limited to, azacyclopentane ring, azacyclohexane ring, azacycloheptane ring and the like.

In the present invention, the term "aryl" means a hydrocarbyl moiety containing one or more aromatic rings. For example, the term "$C_6$-$C_{12}$ aryl" refers to an aromatic ring group with 6 to 12 carbon atoms that does not contain heteroatoms in the ring, such as phenyl, naphthyl and the like. The term "$C_6$-$C_{10}$ aryl" has a similar meaning. Examples of aryl include, but are not limited to, phenyl (Ph), naphthyl, pyrenyl, anthracenyl, and phenanthryl.

In the present invention, the term "heteroaryl" means a moiety containing one or more aromatic rings with at least one heteroatom (such as N, O or S), for example, the term "3-12 membered heterocyclyl" means a saturated or unsaturated 3-12 membered ring group containing 1 to 3 heteroatoms selected from oxygen, sulfur and nitrogen on the ring, such as dioxolyl and the like. The term "3-7 membered heterocyclyl" has a similar meaning. Examples of heteroaryl groups include furyl, fluorenyl, pyrrolyl, thienyl, oxazolyl, imidazolyl, thiazolyl, pyridyl, pyrimidinyl, quinazolinyl, quinolinyl, isoquinolinyl, and indolyl.

In the present invention, the term "heterocyclyl" means a cyclic group containing at least one ring heteroatom (such as N, O or S), such as furyl, pyrrolyl, thienyl, oxazolyl, imidazolyl, thiazolyl, pyridyl, quinolinyl, isoquinolinyl, indolyl, pyrimidinyl, tetrahydropyridyl, pyrrolinyl, dihydropyridyl, dihydrofuranyl, dihydrothienyl, pyranyl.

Unless otherwise specified, the alkyl, alkoxy, cycloalkyl, heterocyclyl, and aryl described herein are substituted and unsubstituted groups. Possible substituents on alkyl, alkoxy, cycloalkyl, heterocyclyl and aryl include, but are not limited to: hydroxyl, amino, nitro, cyano, halogen, $C_1$-$C_6$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, $C_1$-$C_6$ alkoxy, aryl, heteroaryl, heteroaryloxy, $C_1$-$C_{10}$ alkylamino, $C_1$-$C_{20}$ dialkylamino, arylamino, diarylamino, $C_1$-$C_{10}$ alkylsulfamoyl, arylsulfamoyl, $C_1$-$C_{10}$ alkylimino, $C_1$-$C_{10}$ alkylsulfoimino, arylsulfoimino, mercapto, $C_1$-$C_{10}$ alkylthio, $C_1$-$C_{10}$ alkylsulfonyl, arylsulfonyl, acylamino, aminoacyl, aminothioacyl, guanidinyl, ureido, cyano, acyl, thioacyl, acyloxy, carboxyl and carboxylate group. On the other hand, cycloalkyl, heterocycloalkyl, heterocycloalkenyl, aryl, and heteroaryl may also be fused to each other.

In the present invention, the substitution is mono-substitution or poly-substitution, and the poly-substitution is di-substitution, tri-substitution, tetra-substitution, or penta-substitution. The di-substitution means that there are two substituents, and so on.

The pharmaceutically acceptable salt of the present invention may be a salt formed by an anion and a positively charged group on the compound of formula I. Suitable anion is chloride, bromide, iodide, sulfate, nitrate, phosphate, citrate, methanesulfonate, trifluoroacetate, acetate, malate, tosylate, tartrate, fumarate, glutamate, glucuronate, lactate, glutarate or maleate ion. Similarly, a salt can be formed from a cation and a negatively charged group on the compound of formula I. Suitable cation includes sodium ion, potassium ion, magnesium ion, calcium ion and ammonium ion, such as tetramethylammonium ion.

In another preferred example, "pharmaceutically acceptable salt" refers to a salt formed by a compound of formula I and an acid selected from the group consisting of hydrofluoric acid, hydrochloric acid, hydrobromic acid, phosphoric acid, acetic acid, oxalic acid, sulfuric acid, nitric acid, methanesulfonic acid, aminosulfonic acid, salicylic acid, trifluoromethanesulfonic acid, naphthalenesulfonic acid, maleic acid, citric acid, acetic acid, lactic acid, tartaric acid, succinic acid, oxalic acid, pyruvic acid, malic acid, glutamic acid, p-toluenesulfonic acid, naphthalenesulfonic acid, ethanesulfonic acid, naphthalenedisulfonic acid, malonic acid, fumaric acid, propionic acid, oxalic acid, trifluoroacetic acid, stearic acid, pamoic acid, hydroxymaleic acid, phenylacetic acid, benzoic acid, glutamic acid, ascorbic acid, p-aminobenzenesulfonic acid, 2-acetoxybenzoic acid and isethionic acid, etc.; or sodium salt, potassium salt, calcium salt, aluminum salt or ammonium salt formed by a compound of formula I and inorganic base; or methylamine salt, ethylamine salt or ethanolamine salt formed by a compound of general formula I and organic base.

Preparation Method

The preparation method of the compound represented by the general formula I of the present invention, the synthetic route is as follows:

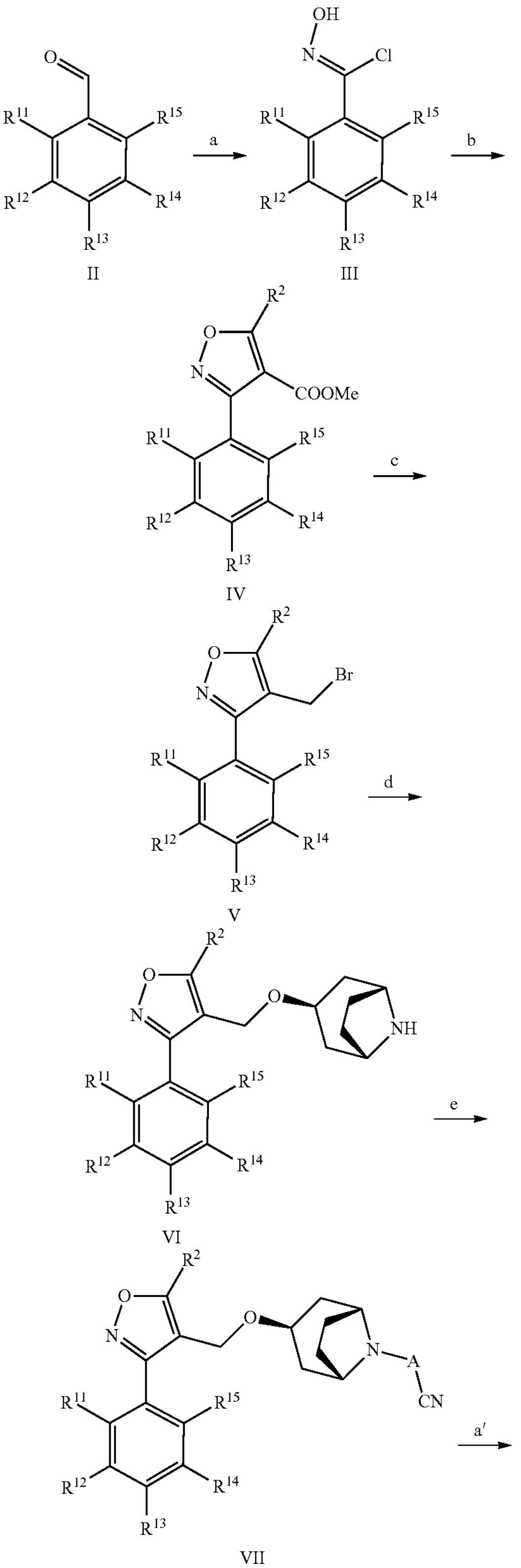

II III IV V VI VII

-continued

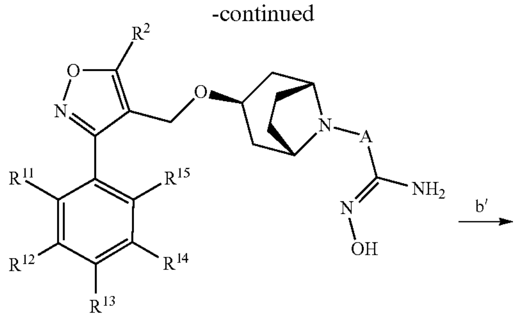

VIII

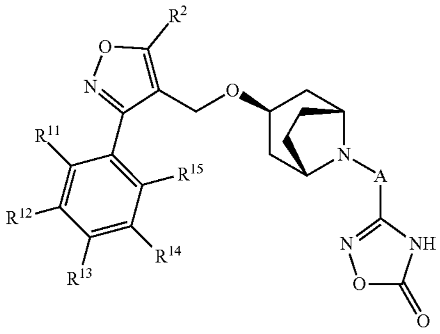

I

The preparation method includes the following steps:

a) reacting substituted benzaldehyde as a starting material with hydroxylamine hydrochloride under the action of an alkali to obtain an intermediate and then chlorinating with N-chlorosuccinimide (NCS) to form a compound represented by the general formula III;

b) reacting the compound represented by the general formula III with the corresponding 3-oxopropionate under an alkali condition to form a compound represented by the general formula IV;

c) reducing the ester in the compound represented by the general formula IV by a reducing agent to generate the corresponding alcohol, and then brominating to form the compound represented by V, d) reacting the compound represented by the general formula V with endo-8-azabicyclio[3.2.1]octan-3-ol under the action of an alkali to form the compound represented by the general formula VI;

e) coupling the compound represented by the general formula VI with Br-A-CN under the catalysis of copper or palladium to obtain a cyano compound represented by the general formula VII;

a') reacting the compound represented by the general formula VII with hydroxylamine hydrochloride under the action of an alkali to produce a compound represented by the general formula VIII;

b') reacting the compound represented by the general formula VIII under the action of phosgene, triphosgene, carbonyl diimidazole or dimethyl carbonate to produce the compound represented by the general formula I.

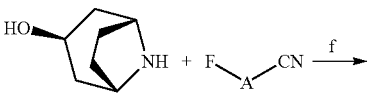

-continued

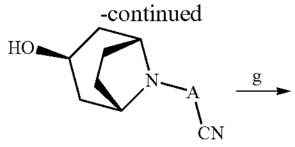

IX

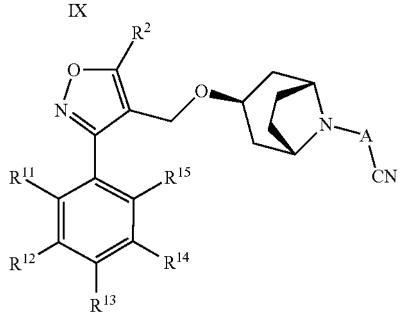

VII

The cyano compound represented by the general formula VII can also be prepared by the above route, including the following steps:

f) substituting the fluorine in F-A-CN with the amino in endo-8-azabicyclio[3.2.1]octan-3-ol in the presence of an alkali to generate compound IX;

g) directly reacting a compound represented by the general formula V with the prepared IX under the action of an alkali to form the compound represented by the general formula VI;

wherein $R^2$, $R^{11}$, $R^{12}$, $R^{13}$, $R^{14}$, $R^{15}$ and A ring are defined as above.

The alkali in steps a), b), d), a'), f) and g) is selected from triethylamine, diisopropylethylamine, pyridine, 4-dimethylaminopyridine, 1,8-diazabicycloundec-7-ene, sodium carbonate, potassium carbonate, lithium hydroxide, sodium hydroxide, potassium hydroxide, sodium methoxide, sodium ethoxide, potassium ethoxide, potassium tert-butoxide, sodium tert-butoxide, butyl lithium, lithium diisopropylamide.

The alkali in step b) is selected from the group consisting of triethylamine, diisopropylethylamine, pyridine, DBU, sodium carbonate, potassium carbonate, lithium hydroxide, sodium hydroxide, potassium hydroxide, sodium methoxide, sodium ethoxide, and potassium ethoxide.

The reducing agent in step c) is selected from the group consisting of sodium borohydride, sodium triacetoxyborohydride, sodium cyanoborohydride, lithium aluminum hydride, diisopropyl aluminum hydride, and borane.

The copper catalyst in step e) is cuprous iodide, cuprous oxide, and cuprous sulfate; the palladium catalyst is palladium acetate, tetrakis(triphenylphosphine) palladium, bis(acetonitrile) palladium (II) chloride, dichloride palladium, tris(dibenzylideneacetone)dipalladium, bistriphenylphosphorus palladium dichloride, tris(dibenzylideneacetone)dipalladium-chloroform adduct, 1,1'-bis(diphenylphosphino) ferrocene palladium(II) dichloride.

Pharmaceutical Composition

The present invention also provides a pharmaceutical composition, which contains active ingredient in a safe and effective amount, and a pharmaceutically acceptable carrier.

The "active ingredient" in the present invention refers to the compound of formula I in the present invention.

The "active ingredient" and pharmaceutical composition of the present invention are used in the manufacture of a medicament for treating FXR-related diseases. The "active ingredient" and pharmaceutical composition of the present invention can be used as FXR agonist. In another preferred example, it is used in the manufacture of a medicament for preventing and/treating a disease regulated by FXR agonist.

"Safe and effective amount" means that the amount of the active ingredient is sufficient to significantly improve the condition without causing serious side effects. Generally, the pharmaceutical composition contains 1-2000 mg of active ingredient/dose, more preferably, 10-200 mg of active ingredient/dose. Preferably, the "one dose" is a tablet.

"Pharmaceutically acceptable carrier" refers to one or more compatible solid or liquid fillers or gel substances, which are suitable for human use, and must have sufficient purity and sufficiently low toxicity. "Compatibility" herein means that each component in the composition can be blended with each other and can be blended with the active ingredient of the present invention without significantly reducing the efficacy of the active ingredient.

Examples of pharmaceutically acceptable carriers include cellulose and derivatives thereof (such as sodium carboxymethyl cellulose, sodium ethyl cellulose, cellulose acetate, etc.), gelatin, talc, solid lubricant (such as stearic acid, magnesium stearate), calcium sulfate, vegetable oil (such as soybean oil, sesame oil, peanut oil, olive oil, etc.), polyol (such as propylene glycol, glycerin, mannitol, sorbitol, etc.), emulsifier (such as Tween®), Wetting agent (such as sodium lauryl sulfate), coloring agent, flavoring agent, stabilizer, antioxidant, preservative, pyrogen-free water and the like.

The administration method of the active ingredient or the pharmaceutical composition of the present invention is not particularly limited, and representative administration methods include (but are not limited to): oral administration, intratumoral administration, rectal administration, parenteral (intravenous, intramuscular, or subcutaneous) administration and the like.

Solid dosage forms for oral administration include capsules, tablets, pills, powders and granules.

Liquid dosage forms for oral administration include pharmaceutically acceptable emulsions, solutions, suspensions, syrups or tinctures. In addition to the active ingredient, the liquid dosage form may contain inert diluents conventionally used in the art, such as water or other solvents, solubilizers and emulsifiers, for example, ethanol, isopropanol, ethyl carbonate, ethyl acetate, propylene glycol, 1,3-butanediol, dimethylformamide and oils, especially cottonseed oil, peanut oil, corn germ oil, olive oil, castor oil and sesame oil or mixtures of these substances. In addition to these inert diluents, the composition may also contain adjuvants such as wetting agents, emulsifying agents and suspending agents, sweetening agents, flavoring agents and perfumes.

In addition to the active ingredient, the suspension may contain suspending agent, for example, ethoxylated isostearyl alcohol, polyoxyethylene sorbitol and dehydrated sorbitan ester, microcrystalline cellulose, aluminum methoxide and agar, or mixtures of these substances, and the like.

The composition for parenteral injection may contain physiologically acceptable sterile aqueous or non-aqueous solutions, dispersions, suspensions or emulsions, and sterile powders for reconstitution into sterile injectable solutions or dispersions. Suitable aqueous and non-aqueous carriers, diluents, solvents or excipients include water, ethanol, polyol and suitable mixtures thereof.

The compound of the present invention can be administered alone or in combination with other therapeutic drugs (such as hypolipidemic drugs).

When the pharmaceutical composition is used, a safe and effective amount of the compound of the present invention is administered to the mammal (such as a human) in need of treatment, wherein the dosage at which the drug is administered is the pharmaceutically effective administration dosage. For a person of 60 kg body weight, the daily dose is usually 0.1-200 mg, and 0.5-5 mg is preferred. Certainly, the specific dosage should be determined by considering factors such as the route of administration, the patient's health status, etc., which are within the skill range of a skilled physician.

The present invention will be further described below in conjunction with specific examples. It should be understood that these examples are only used to illustrate the present invention and not to limit the scope of the present invention. The experimental methods without specific conditions in the following examples generally follow the conventional conditions (e.g. the conditions described in Sambrook et al., Molecular Cloning: Laboratory Manual (New York: Cold Spring Harbor Laboratory Press, 1989)) or the conditions recommended by the manufacturer. Unless stated otherwise, percentages and parts are percentages by weight and parts by weight.

Unless otherwise defined, all professional and scientific terms used herein have the same meaning as those familiar to the skilled in the art. In addition, any methods and materials similar to or equivalent to those described can be applied to the method of the present invention. The preferred implementation methods and materials described herein are for demonstration purposes only.

The instruments and main experimental materials used are as follows.

The reagents and anhydrous solvents used were purchased from Chinese commercial companies. Unless otherwise specified, they were used directly. $^{1}H$ and $^{13}C$ NMR were measured by BrukerAM-400 and Varian Mercury plus-400 nuclear magnetic resonance instruments, and mass spectrometry was measured by Agilent 6230 mass spectrometer and 200-300 mesh of column chromatography silica gel (Qingdao Ocean Chemical Factory), HSGF254 TLC plate (Yantai Chemical Industry Research Institute).

Route 1

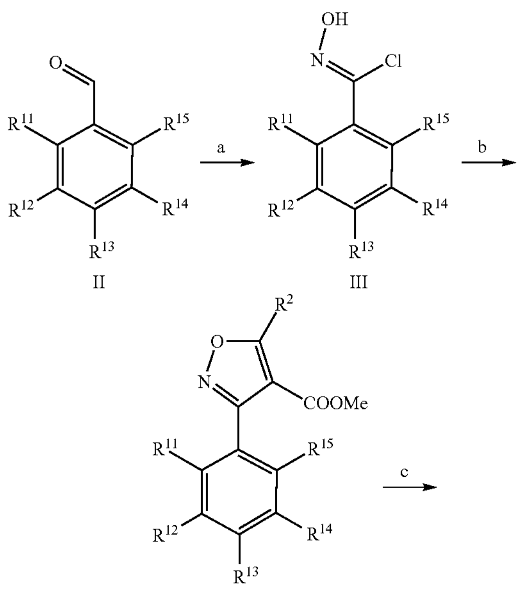

II

III

IV

-continued
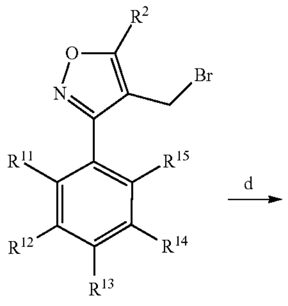
V
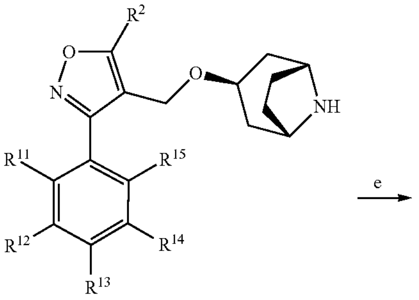
VI
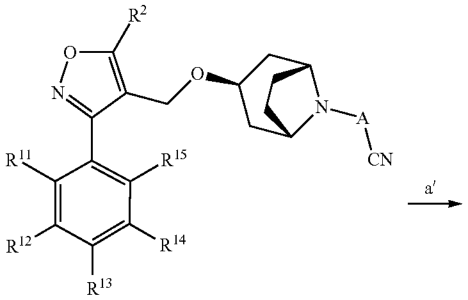
VII
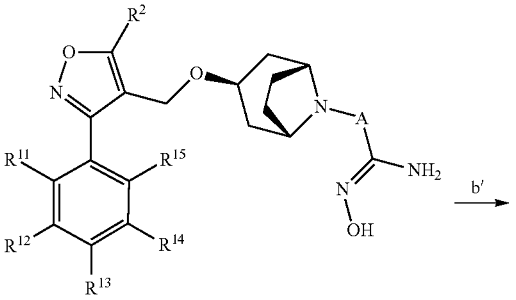
VIII
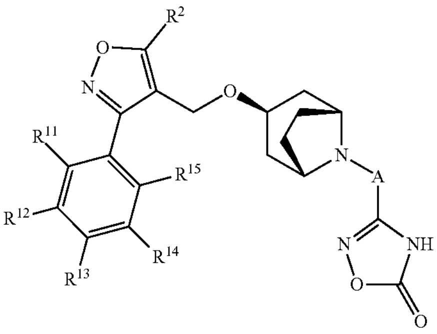
I
Route 2
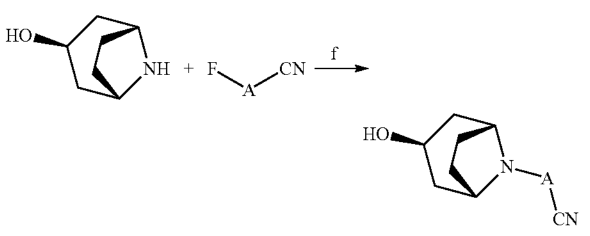
IX
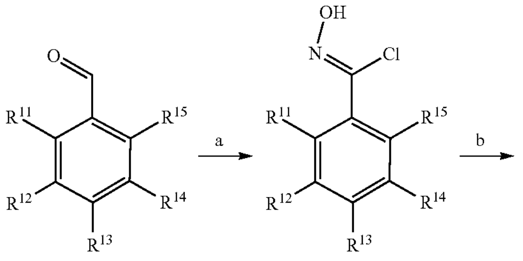
II
III
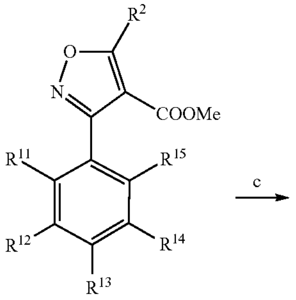
IV
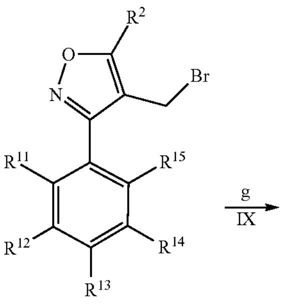
V
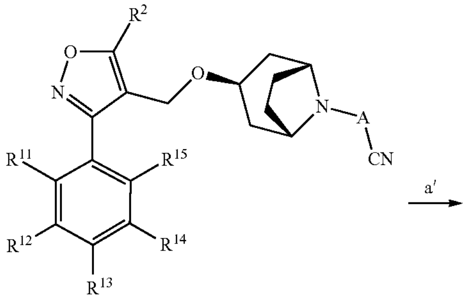
VII -continued

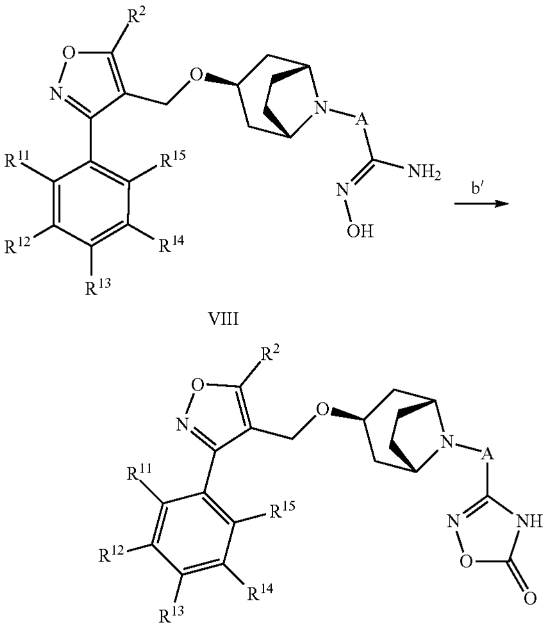

VIII

I

Example 1

1

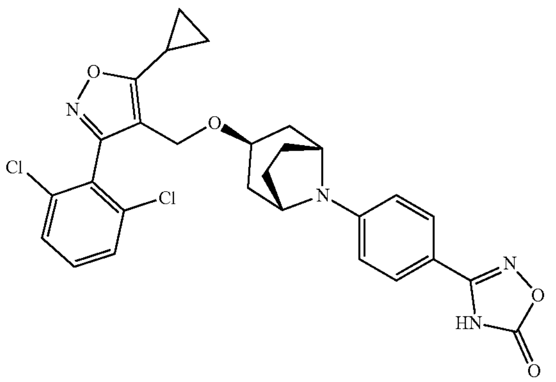

Synthesis of Intermediate V-1

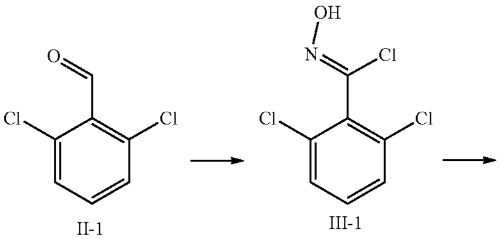

II-1

III-1

-continued

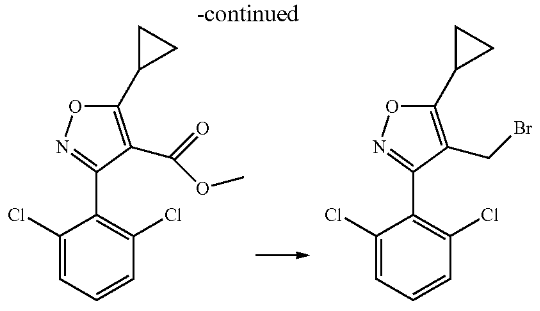

IV-1

V-1

At 0° C., an aqueous potassium carbonate solution (3 N, 182 mmol) was added dropwise to a stirring solution of hydroxylamine hydrochloride (182 mmol) in ethanol (100 mL), 2,6-dichlorobenzaldehyde (20 g, 114 mmol) was dissolved in 100 ml of ethanol, and then added to the hydroxylamine solution. The temperature was raised to 90° C. and the mixture was reacted for two hours. The mixture was cooled to room temperature and then concentrated to a solid. A water/ethanol (1000 mL/100 mL) solution was added and the solid was stirred to break up, filtered, and dried under vacuum at 50° C. overnight to obtain a compound intermediate (18.4 g). This intermediate was dissolved in N,N-dimethylformamide (50 mL), and added dropwise to N-chlorosuccinimide (97 mmol) solution in N,N-dimethylformamide (100 mL) at 0° C. and stirred overnight. The reaction solution was poured into ice water at 0° C., and then extracted with methyl tert-butyl ether (200 mL each time, 3 times in total), the organic phase was washed with saturated brine, and concentrated to obtain a crude product. N-hexane (600 mL) was added to the flask containing the crude product, stirred with a magnetic stir bar, filter, and the solid was dried under vacuum (30° C.) to obtain Intermediate III-1 (18.3 g, yield 73%). $^1H$ NMR (400 MHz, $CDCl_3$) δ 7.43-7.39 (m, 2H), 7.39-7.33 (m, 1H).

Triethylamine (8.2 g) was added to methyl 3-cyclopropyl-3-oxopropionate (82 mmol) and stirred for 30 minutes. Then the mixture was cooled to 10° C., and a solution of III-1 (18.3 g, 82 mmol) in absolute ethanol (80 mL) was added dropwise (internal temperature did not exceed 30° C.), and the reaction was kept overnight at room temperature. The reaction solution was diluted by adding ethyl acetate (100 mL), washed with water, and the aqueous phase was extracted with ethyl acetate (100 mL each time, 3 times in total). The organic phases were mixed, washed with saturated brine, and concentrated. 100 mL of ether was added to the concentrate and stirred, and the solvent was removed under vacuum to obtain solid product IV-1 (21.6 g, yield 84%). $^1H$ NMR (400 MHz, $CDCl_3$) δ 7.43-7.39 (m, 2H), 7.39-7.33 (m, 1H), 3.72 (s, 3H), 2.21-2.09 (m, 1H), 1.35-1.28 (m, 2H), 1.25-1.18 (m, 2H).

IV-1 (21.6 g, 69 mmol) was dissolved in tetrahydrofuran (140 mL) and cooled to 0° C. A solution of diisobutylaluminum hydride (1.5 M, 102 mL) in toluene was slowly added and the reaction solution is stirred at room temperature for 6 h. The reaction solution was slowly poured into ice water, and 1M aqueous hydrochloric acid solution was added to adjust the pH to about 2. The mixture was extracted with ethyl acetate (100 mL each time, three times in total), concentrated, and subjected to column chromatography to obtain the intermediate alcohol. This intermediate and triphenyl phosphine (59 mmol) were dissolved in dichloromethane (60 mL) and cooled to 0° C., and a solution of carbon tetrabromide (62 mmol) in dichloromethane (60 mL) was added dropwise under the protection of nitrogen and reacted at room temperature for 4 h. The solvent was removed from the reaction solution to obtain an oily substance, which was subjected to column chromatography to obtain intermediate V-1 (15.3 g, yield 96%). $^1$H NMR (400 MHz, $CDCl_3$) δ 7.49-7.44 (m, 2H), 7.43-7.37 (m, 1H), 4.25 (d, J=1.3 Hz, 2H), 2.21-2.09 (m, 1H), 1.35-1.28 (m, 2H), 1.25-1.18 (m, 2H).

Example 1 Synthesis

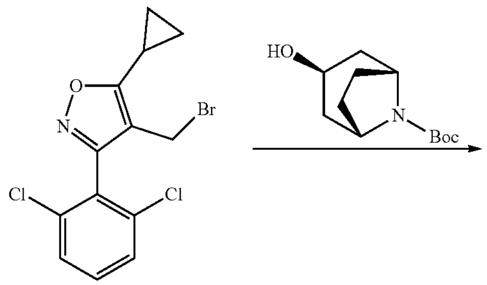

V-1

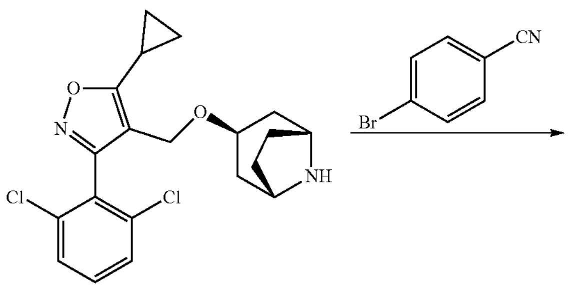

VI-1

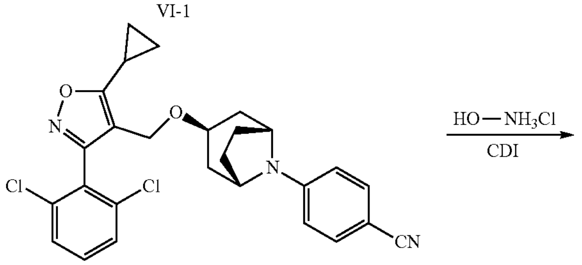

VII-1

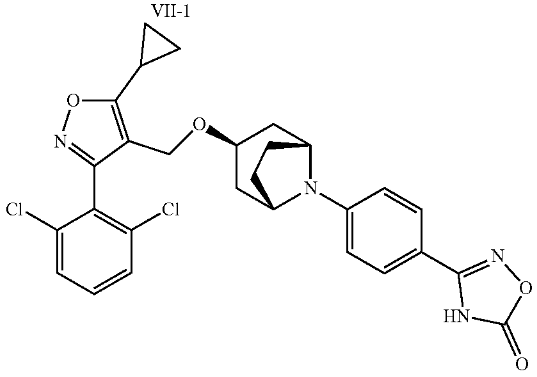

1

At 0° C., potassium tert-butanol (6.5 mmol) was added to a solution of tert-Butyl 3-endo-3-hydroxy-8-azabicyclo[3.2.1]octane-8-carboxylate (1.5 g, 6.5 mmol) in anhydrous tetrahydrofuran (20 mL) and stirred for 30 minutes. And then a solution of V-1 (4.3 mmol) in anhydrous tetrahydrofuran (5 mL) was added dropwise and reacted for 8 hours. Water (20 mL) was added to the reaction solution, which was then extracted with ethyl acetate (15 mL each time, 3 times in total). The organic phase was washed with saturated salt water, concentrated, and subjected to column chromatography to obtain the crude intermediate. The intermediate was dissolved in dichloromethane (8 mL) and cooled to 0° C. Trifluoroacetic acid (8 mL) was added dropwise and stirred at room temperature for 3 h. The solvent was removed under vacuum and ethyl acetate (20 mL) was added to dissolve the residue, which was then washed with 2N sodium hydroxide solution and saturated salt water. The solvent was removed to obtain the intermediate VI-1 (1.1 g, yield 72%). $^1$H NMR (400 MHz, $CDCl_3$) δ 7.42-7.39 (m, 2H), 7.36-7.31 (m, 1H), 4.27-4.18 (m, 2H), 4.10-3.96 (m, 2H), 3.53 (t, J=4.7 Hz, 1H), 2.16-1.60 (m, 9H), 1.26-1.05 (m, 4H).

The intermediate VI-1 (1.0 g, 2.7 mmol), 3-bromobenzonitrile (4.1 mmol), sodium tert-butanol (5.4 mmol), palladium acetate (0.14 mmol), 1,1'-binaphthyl-2,2'-diphenyl phosphine (0.27 mmol) were added to the round bottom flask, and toluene (80 mL) was added. The mixture was heated to reflux, and reacted overnight. The reaction solution was cooled to room temperature, added with water, extracted, concentrated, and subjected to column chromatography to obtain the intermediate VII-1 (0.56 g, yield 43%). $^1$H NMR (400 MHz, $CDCl_3$) δ 7.47-7.34 (m, 5H), 6.65 (d, J=8.9 Hz, 2H), 4.26 (s, 2H), 4.13-4.10 (m, 2H), 3.46-3.41 (m, 1H), 2.17-1.81 (m, 7H), 1.66-1.11 (m, 6H).

VII-1 (0.4 g, 0.9 mmol), hydroxylamine hydrochloride (2.3 mmol), and anhydrous ethanol (5 mL) were added into a round-bottomed flask and stirred. Triethylamine (2.3 mmol) was slowly added, heated to 80° C., and reacted for 4 hours. The mixture was cooled to room temperature and the solvent was removed. The residue was dissolved in ethyl acetate (15 mL), and washed with water and saturated salt water. The organic phase was concentrated and subjected to silica gel column chromatography to obtain the intermediate VIII-1 (0.42 g, yield 95%).

VIII-1 (0.41 g, 0.83 mmol), N,N'-carbonyl diimidazole (1.0 mmol), 1,4-dioxane (4 mL) were added into a round bottom flask. And then 1,8-diazabicyclo[5.4.0]undecano-7-ene (0.91 mmol) was added, heated to 100° C. and reacted for 3 hours. The reaction solution was cooled to room temperature and diluted with water (5 mL. The pH value was adjusted to about 2 with 1M aqueous hydrochloric acid solution, and then the mixture was extracted with ethyl acetate (4 mL each time, 3 times in total). The combined organic phase was washed with saturated salt water and concentrated to obtain the crude product, which was then subjected to silica gel column chromatography to obtain the final product 1 (0.29 g yield 64%).

$^1$H NMR (400 MHz, $CDCl_3$) δ 7.60 (d, J=8.8 Hz, 2H), 7.44-7.32 (m, 3H), 6.70 (d, J=9.0 Hz, 2H), 4.25 (s, 2H), 4.12-4.08 (m, 2H), 3.42 (s, 1H), 2.18-1.82 (m, 7H), 1.61 (d, J=14.4 Hz, 2H), 1.26-1.10 (m, 4H). MS(ESI, m/z): 553[M+H]$^+$.

Example 2

2

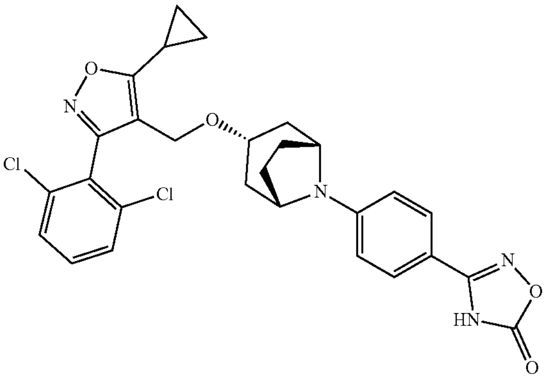

Example 2 compound was prepared from the intermediate VI-1 through route 1 by referring to the operation of Example 1. The synthesis route is as follows.

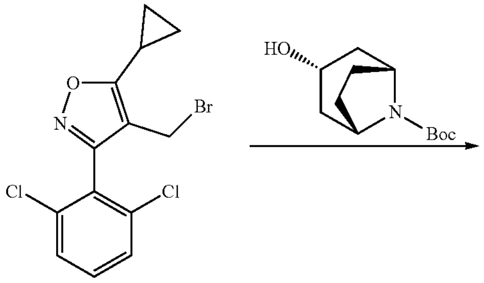

V-1

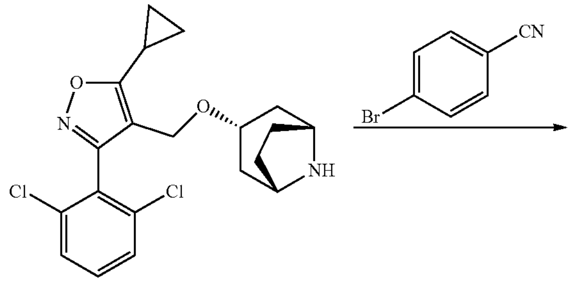

VI-2

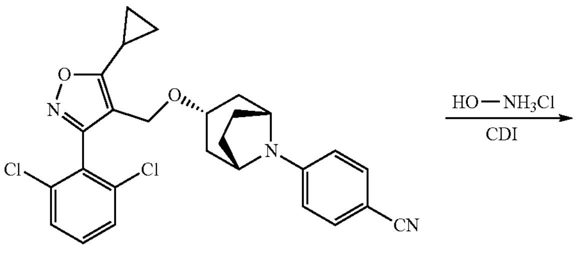

VII-2

-continued

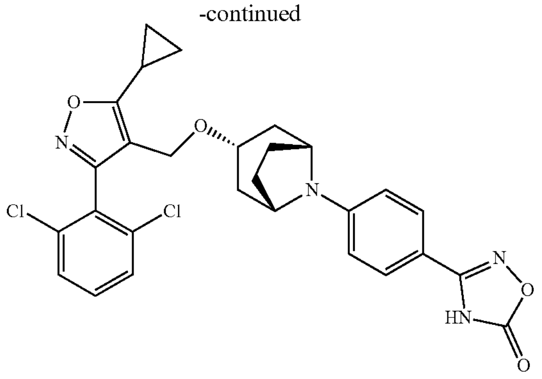

2

Compound 2 was synthesized from the raw material V-1 according to the synthetic method of compound 1.

Oil intermediate VI-1, yield 56%, $^1$H NMR (500 MHz, Chloroform-d) δ 7.45-7.41 (m, 2H), 7.39-7.34 (m, 1H), 4.32-4.24 (m, 2H), 4.01-3.91 (m, 2H), 3.59-3.49 (m, 1H), 2.19-2.08 (m, 3H), 1.93-1.65 (m, 6H), 1.28-1.11 (m, 4H).

White solid VII-2, yield 88%, $^1$H NMR (500 MHz, Chloroform-d) δ 7.50-7.45 (m, 2H), 7.38-7.34 (m, 2H), 7.31-7.26 (m, 1H), 6.71-6.65 (m, 2H), 4.31-4.20 (m, 4H), 3.81-3.71 (m, 1H), 2.13-2.02 (m, 3H), 1.78-1.66 (m, 4H), 1.47-1.39 (m, 2H), 1.30-1.08 (m, 4H).

White solid 2, yield 52%, $^1$H NMR (500 MHz, DMSO-$d_6$) δ 7.63 (d, J=8.8 Hz, 2H), 7.52-7.48 (m, 2H), 7.48-7.43 (m, 1H), 6.86 (d, J=8.8 Hz, 2H), 4.35-4.27 (m, 2H), 4.21 (s, 2H), 3.76-3.66 (m, 1H), 2.34-2.23 (m, 1H), 1.94-1.58 (m, 6H), 1.20-1.03 (m, 6H). MS(ESI, m/z): 553[M+H]$^+$.

Example 3

3

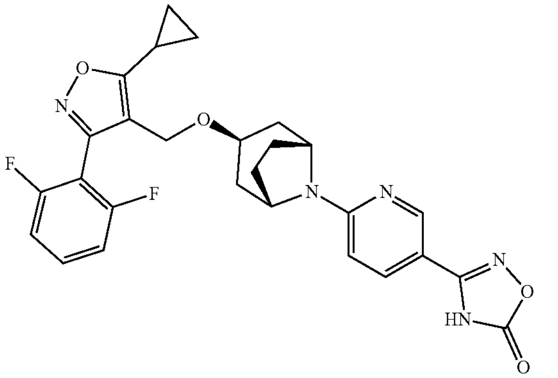

Synthesis of Intermediate V-3

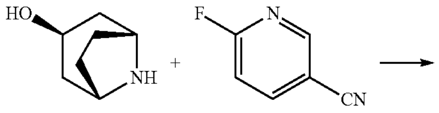

-continued

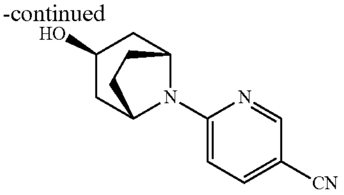

IX-3

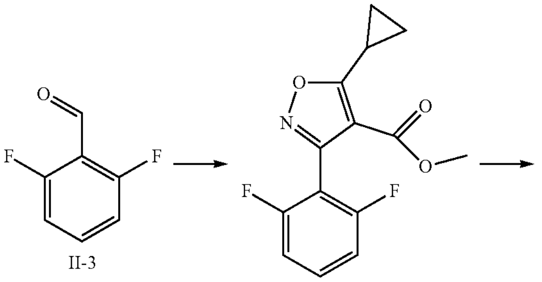

II-3 IV-3

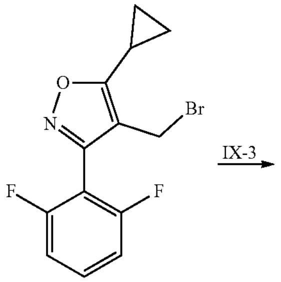

V-3

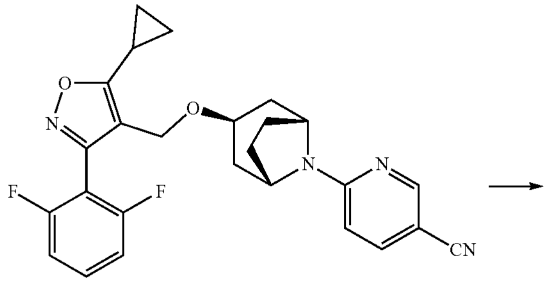

VII-3

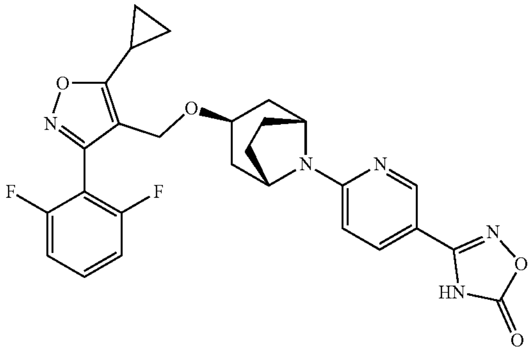

3

6-fluoro-3-cyanopyridine (2 g, 16.5 mmol), endo-8-azabicyclo[3.2.1]octan-3-ol (18.2 mmol), anhydrous potassium carbonate (41.3 mmol) and DMSO (16 mL) were added into a round bottom flask, heated to 130° C., and reacted for 12 h. The mixture was cooled to room temperature, added with 30 mL of water and filtered. The solid was washed with water to obtain intermediate IX-3 (3.2 g, yield 93%) as a white solid, yield 94%, NMR (400 MHz, $CDCl_3$) δ 8.41 (d, J=1.8 Hz, 1H), 7.58 (dd, J=9.0, 2.3 Hz, 1H), 6.49 (d, J=8.9 Hz, 1H), 4.91-4.26 (m, 2H), 4.12 (t, J=4.7 Hz, 1H), 2.39 (d, J=7.3 Hz, 2H), 2.18-1.81 (m, 6H).

Compound V-3 was synthesized from raw material II-3 according to the synthetic method of compound V-1.

White solid IV-3, yield 64%. $^1$H NMR (400 MHz, $CDCl_3$) δ 7.43-7.34 (m, 1H), 7.00-6.91 (m, 2H), 3.69 (s, 3H), 2.92-2.83 (m, 1H), 1.36-1.31 (m, 2H), 1.25-1.20 (m, 2H).

Colorless liquid V-3, yield 82%. $^1$H NMR (400 MHz, $CDCl_3$) δ 7.54-7.44 (m, 1H), 7.11-7.04 (m, 2H), 4.33 (s, 2H), 2.20-2.08 (m, 1H), 1.34-1.17 (m, 4H).

Compound intermediate VII-3 was synthesized from the raw materials V-3 and IX-3 according to the synthetic method of compound VII-1. White solid, yield 51%, $^1$H NMR (400 MHz, $CDCl_3$) δ 8.35 (d, J=2.1 Hz, 1H), 7.52 (dd, J=9.0, 2.1 Hz, 1H), 7.47-6.94 (m, 3H), 6.42 (d, J=9.0 Hz, 1H), 4.75-4.18 (m, 4H), 3.48 (t, J=4.5 Hz, 1H), 2.16-1.81 (m, 7H), 1.69-1.08 (m, 6H).

Compound 3 was synthesized from the raw material VII-3 according to the synthetic method of compound 1. White solid, yield 71%, $^1$H NMR (400 MHz, DMSO) δ 8.48 (d, J=2.4 Hz, 1H), 7.81-7.61 (m, 3H), 7.30 (t, J=8.0 Hz, 2H), 6.79 (d, J=9.0 Hz, 1H), 4.43 (s, 2H), 4.33 (s, 2H), 3.45 (s, 1H), 2.41-2.26 (m, 1H), 1.87-1.04 (m, 12H). MS(ESI, m/z): 522[M+H]$^+$.

Example 4

4

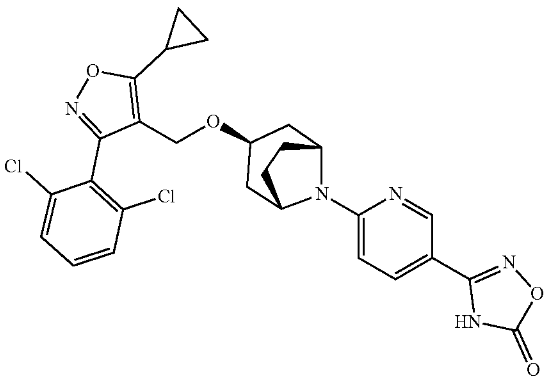

Example 4 was synthesized according to the following route.

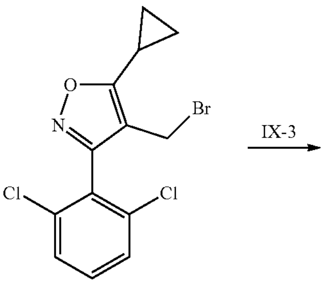

V-1

-continued

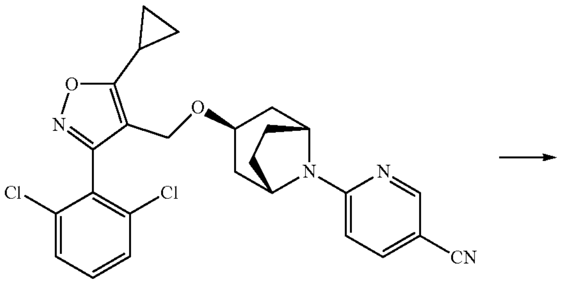

VII-4

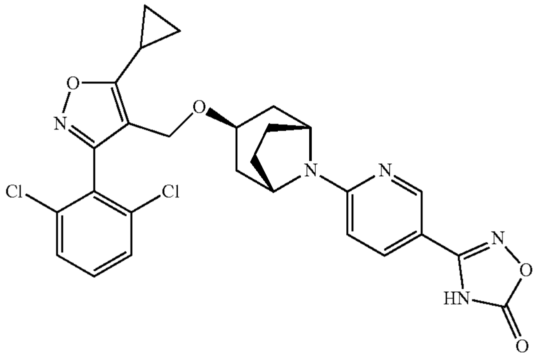

4

Compound intermediate VII-4 was synthesized from raw materials V-1 and IX-3 according to the synthetic method of compound VII-3. White solid, yield 72%; $^{1}$H NMR (400 MHz, $CDCl_3$) δ 8.34 (d, J=2.1 Hz, 1H), 7.51 (dd, J=9.0, 2.1 Hz, 1H), 7.42-7.30 (m, 3H), 6.41 (d, J=9.0 Hz, 1H), 4.63-4.16 (m, 4H), 3.46 (t, J=4.3 Hz, 1H), 2.15-2.07 (m, 1H), 1.97-1.70 (m, 8H), 1.25-1.07 (m, 4H).

The compound 4 was synthesized from the raw material VII-4 according to the synthetic method of compound 1. White solid, yield 47%; $^{1}$H NMR (400 MHz, DMSO) δ 8.43 (d, J=2.4 Hz, 1H), 7.77 (dd, J=9.0, 2.4 Hz, 1H), 7.67-7.52 (m, 3H), 6.75 (d, J=9.0 Hz, 1H), 4.40 (s, 2H), 4.24 (s, 2H), 3.41 (s, 1H), 2.36-2.26 (m, 1H), 1.84-1.03 (m, 12H). MS(ESI, m/z): 554 [M+H]$^{+}$.

Example 5

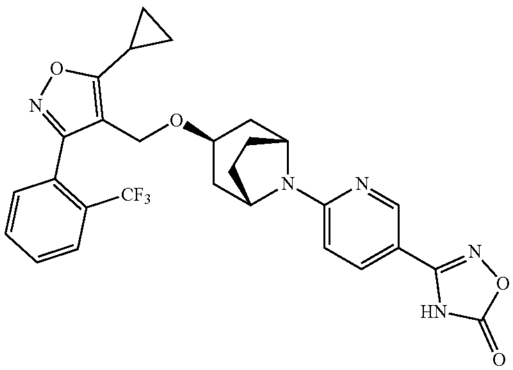

-continued

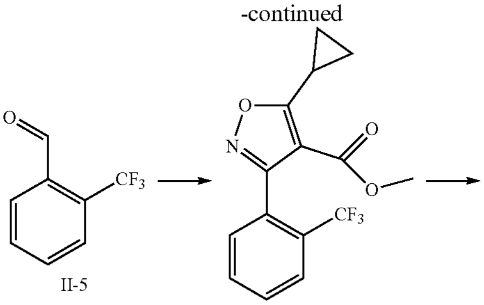

II-5

IV-5

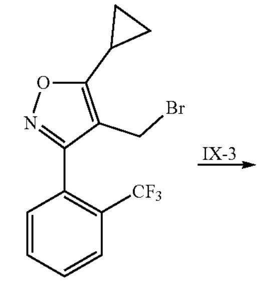

V-5

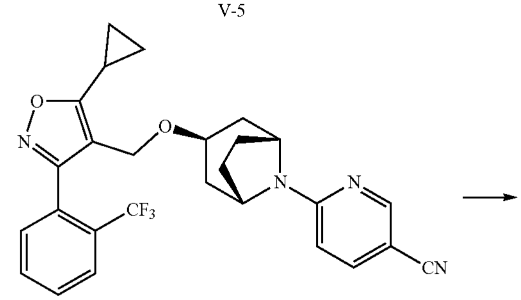

VII-5

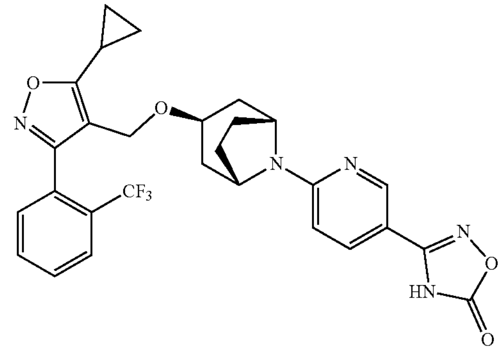

5

Compound 5 was synthesized from raw material II-5 according to the synthetic method of compound 3.

White solid IV-5, yield 58%. $^{1}$H NMR (400 MHz, $CDCl_3$) δ 7.82 (d, J=7.5 Hz, 1H), 7.74-7.59 (m, 2H), 7.56 (d, J=7.5 Hz, 1H), 3.3.73 (s, 3H), 2.19-2.09 (m, 1H), 1.33-1.27 (m, 2H), 1.24-1.15 (m, 2H).

Colorless liquid V-5, yield 88%. $^{1}$H NMR (400 MHz, $CDCl_3$) δ 7.84 (d, J=7.4 Hz, 1H), 7.73-7.61 (m, 2H), 7.57 (d, J=7.4 Hz, 1H), 4.23 (s, 2H), 2.17-2.09 (m, 1H), 1.32-1.27 (m, 2H), 1.23-1.17 (m, 2H).

Compound intermediate VII-5 was synthesized from raw materials V-5 and IX-3 according to the synthetic method of compound VII-3. White solid, yield 63%; $^{1}$H NMR (400 MHz, $CDCl_3$) δ 8.32 (d, J=2.0 Hz, 1H), 7.76 (d, J=7.2 Hz, 1H), 7.63-7.53 (m, 2H), 7.49-7.40 (m, 2H), 6.39 (d, J=9.0

Hz, 1H), 4.57-4.12 (m, 4H), 3.42 (t, J=4.4 Hz, 1H), 2.13-1.69 (m, 9H), 1.20-1.05 (m, 4H).

Compound 5 was synthesized from the raw material VII-5 according to the synthetic method of compound 1. White solid, yield 52%; $^1$H NMR (400 MHz, DMSO) δ 8.45 (d, J=2.4 Hz, 1H), 7.92 (d, J=7.2 Hz, 1H), 7.84-7.60 (m, 4H), 6.79 (d, J=9.1 Hz, 1H), 4.19 (s, 2H), 4.23 (s, 2H), 3.43 (s, 1H), 2.37-2.28 (m, 1H), 1.82-1.62 (m, 8H), 1.17-1.03 (m, 4H). MS(ESI, m/z): 554 [M+H]$^+$.

Example 6

6

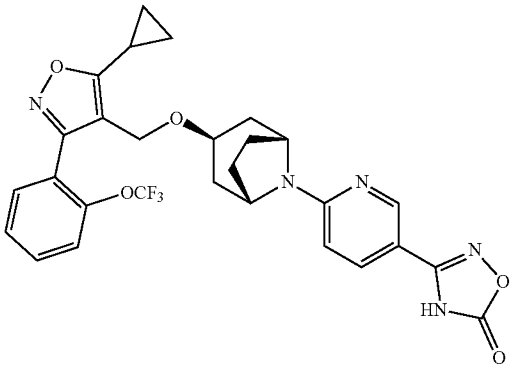

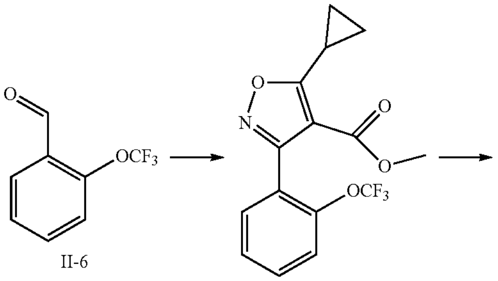

II-6

IV-6

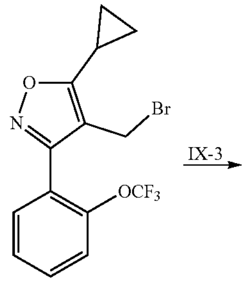

V-6

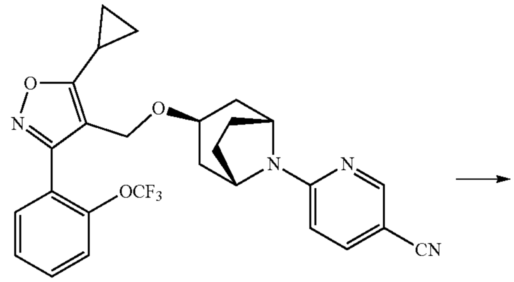

VII-6

-continued

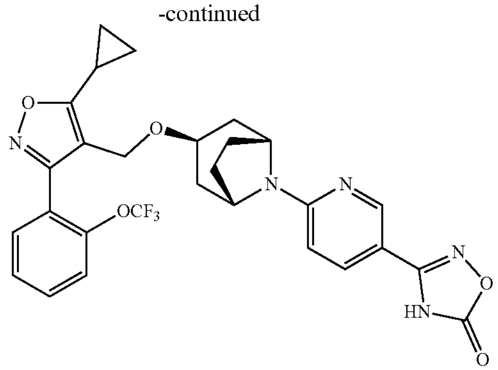

6

Compound V-6 was synthesized from raw material II-56 according to the synthetic method of compound 3.

White solid IV-6, yield 59%. $^1$H NMR (400 MHz, $CDCl_3$) δ 7.66-7.50 (m, 2H), 7.49-7.41 (m, 2H), 3.70 (s, 2H), 2.18-2.10 (m, 1H), 1.31-1.26 (m, 2H), 1.23-1.17 (m, 2H).

Colorless liquid V-6, yield 82%. $^1$H NMR (400 MHz, $CDCl_3$) δ 7.65-7.52 (m, 2H), 7.49-7.40 (m, 2H), 4.36 (s, 2H), 2.18-2.10 (m, 1H), 1.31-1.26 (m, 2H), 1.23-1.17 (m, 2H).

Compound intermediate VII-6 was synthesized from raw materials V-6 and IX-3 according to the synthetic method of compound VII-3. White solid, yield 79%; $^1$H NMR (400 MHz, $CDCl_3$) δ 8.35 (d, J=2.0 Hz, 1H), 7.58-7.35 (m, 5H), 6.44-6.38 (m, 1H), 4.57-4.22 (m, 4H), 3.48 (t, J=4.4 Hz, 1H), 2.16-1.70 (m, 9H), 1.22-1.07 (m, 4H).

Compound 6 was synthesized from the raw material VII-6 according to the synthetic method of compound 1. White solid, yield 51%; $^1$H NMR (400 MHz, DMSO) δ 8.47 (d, J=2.4 Hz, 1H), 7.79 (dd, J=9.0, 2.4 Hz, 1H), 7.69-7.49 (m, 4H), 6.75 (d, J=9.0 Hz, 1H), 4.41 (s, 2H), 4.32 (s, 2H), 3.47 (s, 1H), 2.35-2.26 (m, 1H), 1.86-1.02 (m, 12H). MS(ESI, m/z): 570 [M+H]$^+$.

Example 7

7

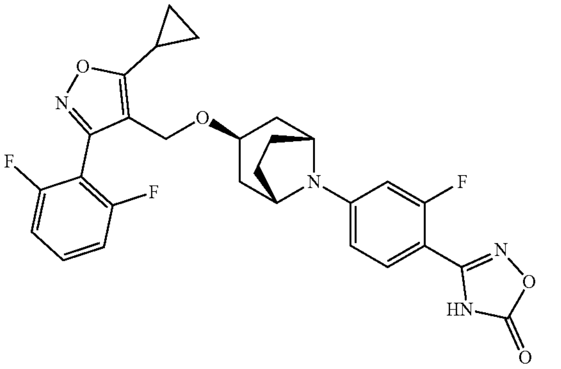

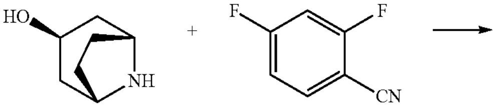

-continued

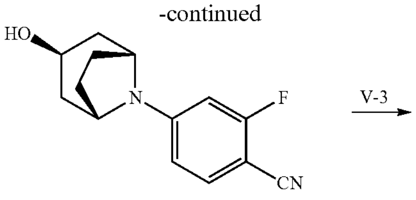

IX-7

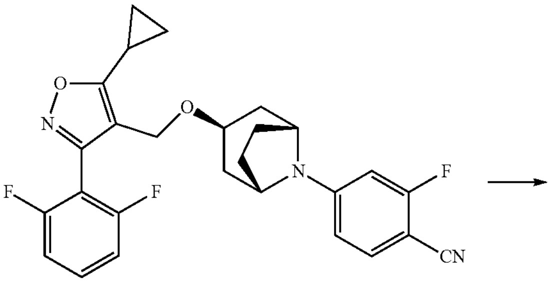

VII-7

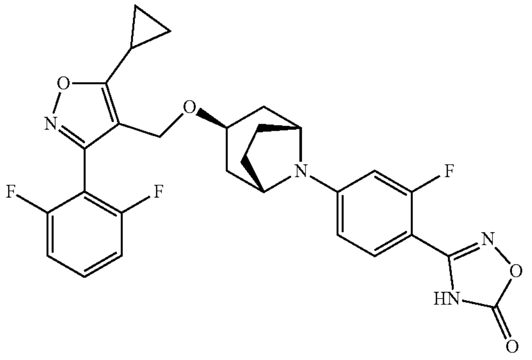

7

The intermediate IX-7 was synthesized from the raw materials endo-8-azabicyclo[3.2.1]octan-3-ol and 2,4-difluorobenzonitrile according to the synthetic method of compound IX-3. White solid, yield 64%; $^1$H NMR (400 MHz, $CDCl_3$) δ 7.36-7.28 (m, 1H), 6.65-6.47 (m, 2H), 4.00-3.90 (m, 1H), 3.76-3.55 (m, 2H), 3.26-3.04 (m, 2H), 2.00-1.53 (m, 4H).

Compound intermediate VII-7 was synthesized from raw materials V-3 and IX-7 according to the synthetic method of compound VII-3. White solid, yield 84%; $^1$H NMR (400 MHz, $CDCl_3$) δ 7.49-7.30 (m, 2H), 7.07-7.00 (m, 2H), 6.44-6.31 (m, 2H), 4.31 (s, 2H), 4.06 (s, 2H), 3.46 (t, J=4.5 Hz, 1H), 2.16-2.08 (m, 1H), 1.99-1.63 (m, 8H), 1.25-1.09 (m, 4H).

Compound 7 was synthesized from the raw material VII-7 according to the synthetic method of compound 1. White solid, yield 60%; $^1$H NMR (400 MHz, DMSO) δ 7.70-7.59 (m, 1H), 7.50 (t, J=8.6 Hz, 1H), 7.29 (t, J=8.0 Hz, 2H), 6.76-6.64 (m, 2H), 4.31 (s, 2H), 4.17 (s, 2H), 3.43 (s, 1H), 2.37-2.26 (m, 1H), 1.83-1.52 (m, 8H), 1.16-1.04 (m, 4H). MS(ESI, m/z): 539 $[M+H]^+$.

Example 8

8

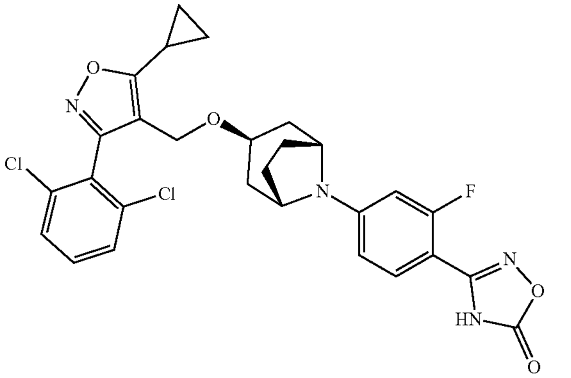

Example 8 was synthesized according to the following route.

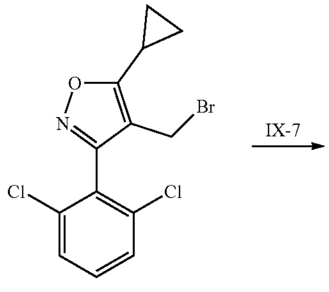

V-1

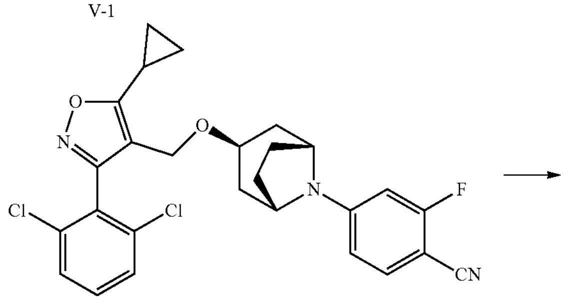

VII-8

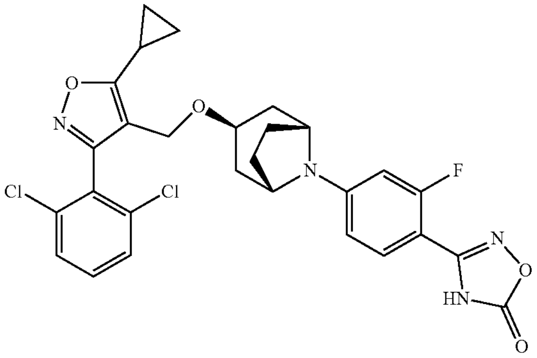

8

Compound intermediate VII-8 was synthesized from raw materials V-1 and IX-7 according to the synthetic method of compound VII-3. White solid, yield 75%; $^1$H NMR (400 MHz, $CDCl_3$) δ 7.46-7.31 (m, 4H), 6.42 (dd, J=8.8, 2.1 Hz, 1H), 6.35 (d, J=12.8 Hz, 1H), 4.26 (s, 2H), 4.07 (s, 2H), 3.46 (t, J=4.4 Hz, 1H), 2.17-1.82 (m, 7H), 1.66 (d, J=14.7 Hz, 2H), 1.29-1.10 (m, 4H).

The compound 7 was synthesized from the raw material VII-7 according to the synthetic method of compound 1. White solid, yield 60%; $^1$H NMR (400 MHz, DMSO) δ 7.65-7.47 (m, 4H), 6.69 (m, 2H), 4.25 (s, 2H), 4.17 (s, 2H), 3.41 (s, 1H), 2.38-2.27 (m, 1H), 1.83-1.54 (m, 8H), 1.16-1.04 (m, 4H). MS(ESI, m/z): 571 [M+H]$^+$.

Example 9

9

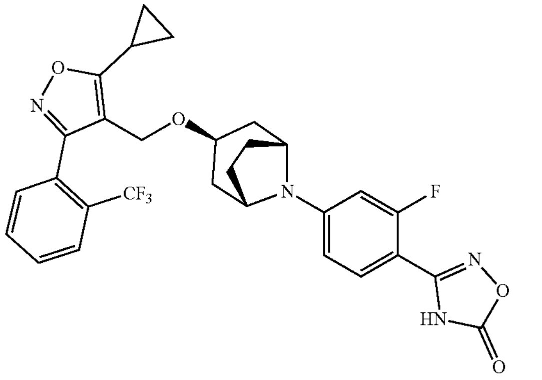

Example 9 was synthesized according to the following route.

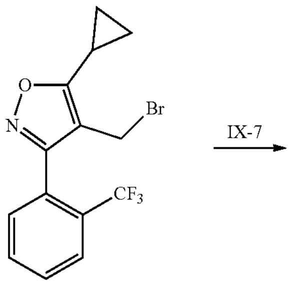

V-5

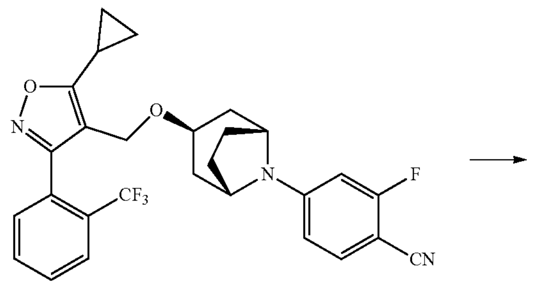

VII-9

-continued

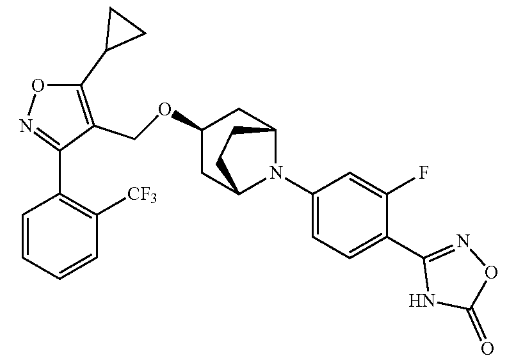

9

Compound intermediate VII-9 was synthesized from raw materials V-5 and IX-7 according to the synthetic method of compound VII-3. White solid, yield 78%; $^1$H NMR (400 MHz, $CDCl_3$) δ 7.84-7.79 (m, 1H), 7.67-7.58 (m, 2H), 7.48-7.32 (m, 2H), 6.45-6.31 (m, 2H), 4.20 (s, 2H), 4.08 (s, 2H), 3.43 (s, 1H), 2.14-1.83 (m, 7H), 1.66 (d, J=14.7 Hz, 2H), 1.29-1.09 (m, 4H).

The compound 9 was synthesized from the raw material VII-9 according to the synthetic method of compound 1. White solid, yield 55%; $^1$H NMR (400 MHz, DMSO) δ 7.91 (d, J=7.6 Hz, 1H), 7.83-7.70 (m, 2H), 7.64-7.47 (m, 2H), 6.75-6.64 (m, 2H), 4.26-4.13 (m, 4H), 3.40 (s, 1H), 2.38-2.24 (m, 1H), 1.83-1.55 (m 8H), 1.18-1.02 (m, 4H). MS(ESI, m/z): 571 [M+H]$^+$.

Example 10

10

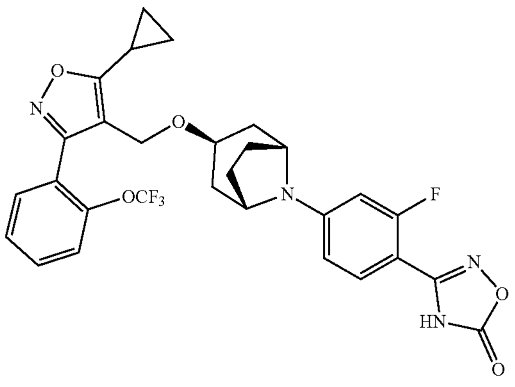

Example 10 was synthesized according to the following route.

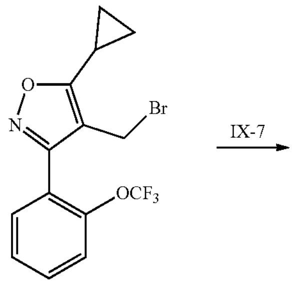

V-6

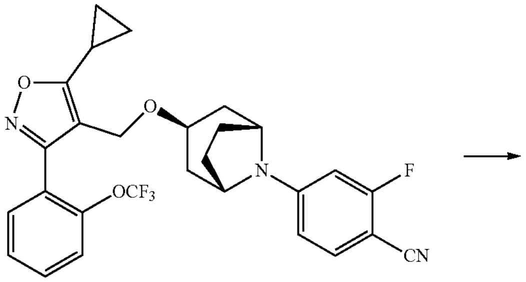

VII-10

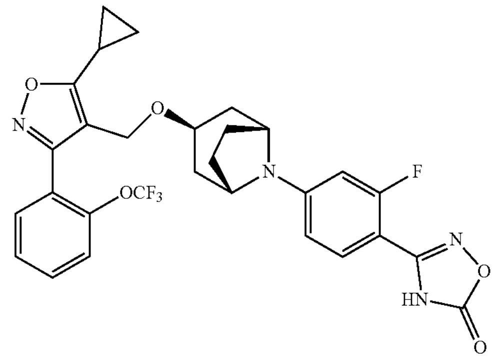

10

Compound intermediate VII-10 was synthesized from raw materials V-6 and IX-7 according to the synthetic method of compound VII-3. White solid, yield 70%; $^{1}$H NMR (400 MHz, $CDCl_3$) δ 7.59-7.52 (m, 2H), 7.44-7.35 (m, 3H), 6.43 (dd, J=8.8, 2.0 Hz, 1H), 6.36 (dd, J=12.8, 2.0 Hz, 1H), 4.36 (s, 2H), 4.08 (s, 2H), 3.48 (t, J=4.4 Hz, 1H), 2.17-1.86 (m, 7H), 1.66 (d, J=14.4 Hz, 2H), 1.27-1.10 (m, 4H).

The compound 10 was synthesized from the raw material VII-10 according to the synthetic method of compound 1. White solid, yield 70%; $^{1}$H NMR (400 MHz, DMSO) δ 7.71-7.46 (m, 5H), 6.77-6.64 (m, 2H), 4.32 (s, 2H), 4.18 (s, 2H), 3.45 (s, 1H), 2.37-2.27 (m, 1H), 1.86-1.56 (m, 8H), 1.17-1.03 (m, 4H). MS(ESI, m/z): 587 [M+H]$^+$.

Example 11

11

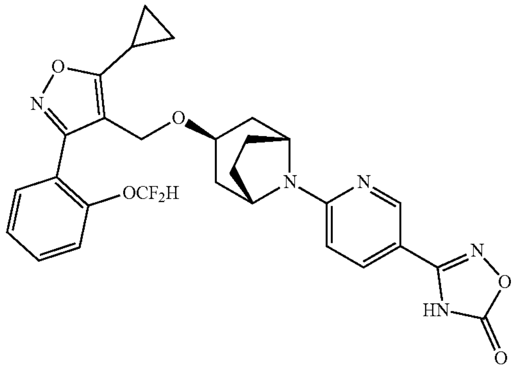

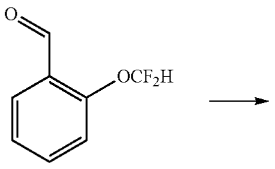

II-11

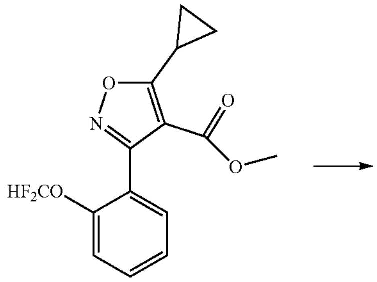

IV-11

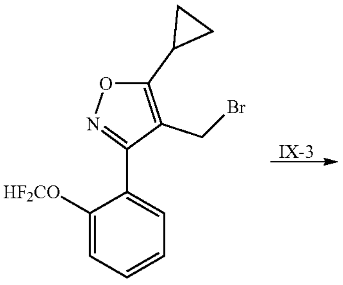

V-11

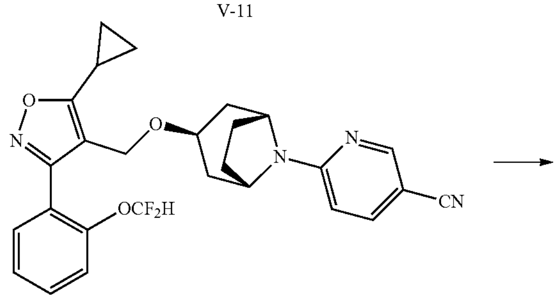

VII-11

-continued

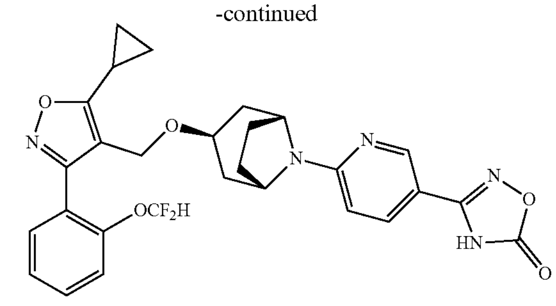

11

Compound V-11 was synthesized from the raw material II-11 according to the synthetic method of synthetic compound V-1.

White solid IV-11, yield 54%. $^1$H NMR (400 MHz, $CDCl_3$) δ 7.52-7.44 (m, 2H), 7.32-7.26 (m, 1H), 7.21 (d, J=8.5 Hz, 1H), 6.46 (t, J=73.7 Hz, 1H), 3.72 (s, 3H), 2.88-2.80 (m, 1H), 1.37-1.32 (m, 2H), 1.26-1.22 (m, 2H).

Colorless liquid V-11, yield 72%. $^1$H NMR (400 MHz, $CDCl_3$) δ 7.60-7.51 (m, 2H), 7.41-7.32 (m, 2H), 6.51 (t, J=73.7 Hz, 1H), 4.38 (s, 2H), 2.18-2.10 (m, 1H), 1.32-1.17 (m, 4H).

Compound intermediate VII-11 was synthesized from raw materials V-11 and IX-3 according to the synthetic method of compound VII-3. White solid, yield 66%. $^1$H NMR (400 MHz, $CDCl_3$) δ 8.37 (d, J=2.0 Hz, 1H), 7.56-7.23 (m, 5H), 6.45 (t, J=74.0 Hz, 1H), 6.42 (d, J=8.8 Hz, 1H), 4.50-4.18 (m, 4H), 3.49 (t, J=4.4 Hz, 1H), 2.16-1.80 (m, 7H), 1.72 (d, J=14.4 Hz, 2H), 1.23-1.06 (m, 4H).

Compound 11 was synthesized from the raw material VII-11 according to the synthetic method of compound 1. White solid, yield 63%. $^1$H NMR (400 MHz, DMSO) δ 8.46 (d, J=2.4 Hz, 1H), 7.79 (dd, J=9.0, 2.4 Hz, 1H), 7.64-7.33 (m, 4H), 7.23 (d, J=74.0 Hz, 1H), 6.78 (d, J=9.0 Hz, 1H), 4.54-4.22 (m, 4H), 3.46 (s, 1H), 2.36-2.26 (m, 1H), 1.86-1.62 (m, 8H), 1.15-1.07 (m, 4H). MS(ESI, m/z): 552[M+H]$^+$.

Example 12

12

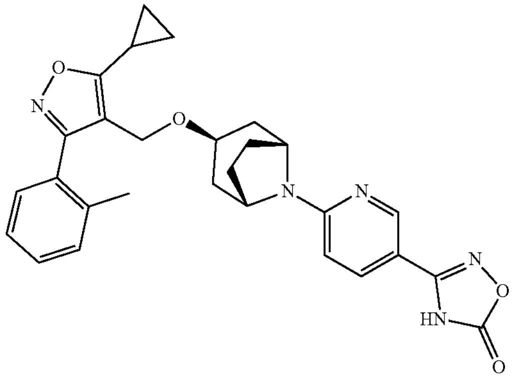

Example 12 was synthesize according to the following route.

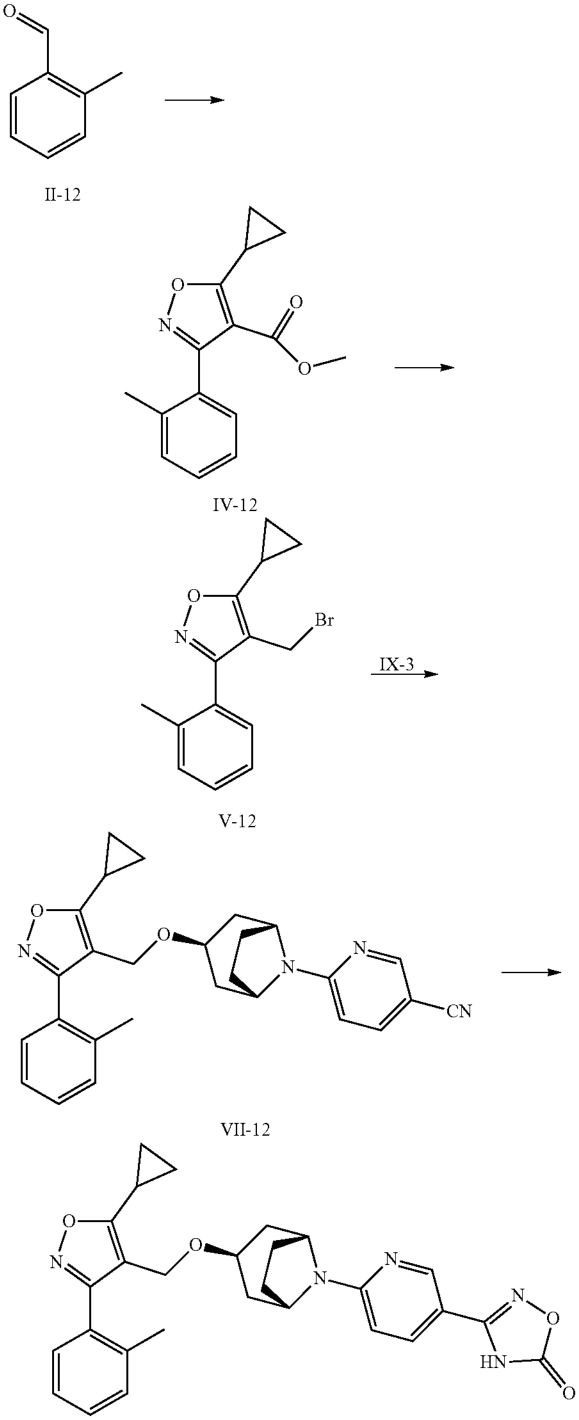

II-12

IV-12

V-12

VII-12

12

Compound V-112 was synthesized from the raw material II-12 according to the synthetic method of synthetic compound V-1.

White solid IV-12, yield 54%. $^1$H NMR (400 MHz, $CDCl_3$) δ 7.42-7.31 (m, 2H), 7.30-7.24 (m, 2H), 3.69 (s, 3H), 2.95-2.87 (m, 1H), 2.23 (s, 3H), 1.42-1.36 (m, 2H), 1.30-1.23 (m, 2H).

Colorless liquid V-12, yield 72%. $^1$H NMR (400 MHz, $CDCl_3$) δ 7.42-7.29 (m, 4H), 4.27 (s, 2H), 2.33 (s, 3H), 2.19-2.10 (m, 1H), 1.32-1.27 (m, 2H), 1.23-1.16 (m, 2H).

Compound intermediate VII-12 was synthesized from raw materials V-12 and IX-3 according to the synthetic method of compound VII-3. White solid, yield 64%. $^1$H NMR (400 MHz, $CDCl_3$) δ 8.38 (d, J=1.8 Hz, 1H), 7.55 (dd, J=8.8, 2.4 Hz, 1H), 7.38-7.23 (m, 4H), 6.44 (d, J=8.8 Hz, 1H), 4.77-4.31 (m, 2H), 4.21 (s, 2H), 3.50 (t, J=4.4 Hz, 1H), 2.31 (s, 3H), 2.17-1.78 (m, 9H), 1.26-1.07 (m, 4H).

Compound 12 was synthesized from the raw material VII-12 according to the synthetic method of compound 1. White solid, yield 69%. $^1$H NMR (400 MHz, DMSO) δ 8.45 (d, J=2.4 Hz, 1H), 7.78 (dd, J=9.0, 2.4 Hz, 1H), 7.37-7.22 (m, 4H), 6.73 (d, J=9.0 Hz, 1H), 4.42 (s, 2H), 4.20 (s, 2H), 3.44 (s, 1H), 2.33-2.21 (m, 4H), 1.91-1.64 (m, 8H), 1.14-1.07 (m, 4H). MS(ESI, m/z): 500 [M+H]$^+$.

Example 13

13

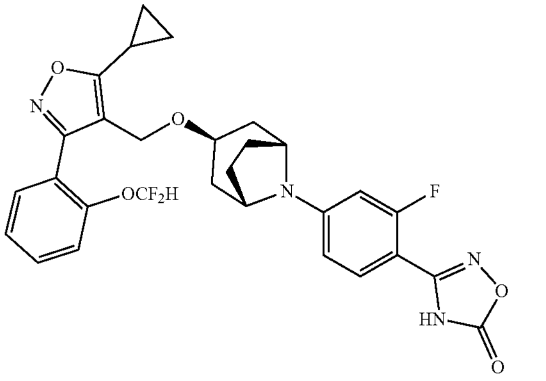

Example 13 was synthesized according to the following route.

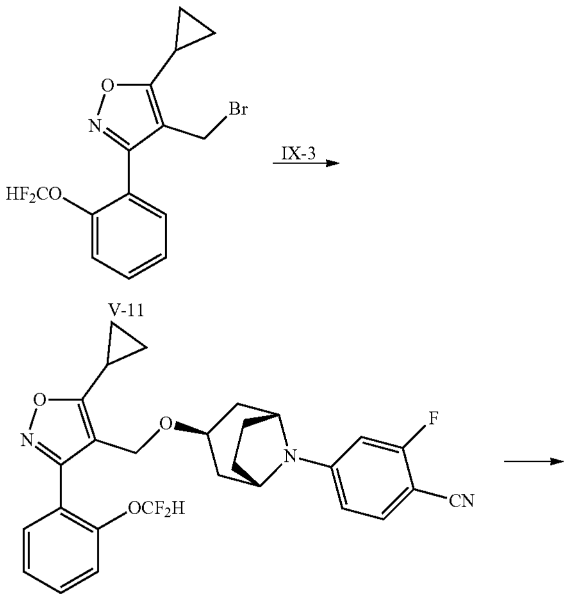

V-11

VII-13

-continued

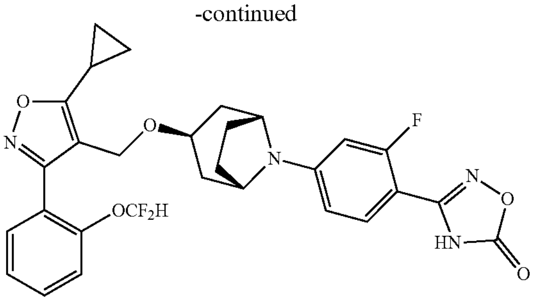

13

Compound intermediate VII-13 was synthesized from raw materials V-11 and IX-3 according to the synthetic method of compound VII-3. White solid, yield 69%. $^1$H NMR (400 MHz, $CDCl_3$) δ 7.56-7.28 (m, 5H), 6.47 (t, J=74.0 Hz, 1H), 6.44-6.31 (m, 2H), 4.33 (s, 2H), 4.08-4.02 (m, 2H), 3.52-3.44 (m, 1H), 2.14-1.84 (m, 7H), 1.64 (d, J=15.0 Hz, 2H), 1.24-1.07 (m, 4H).

Compound 13 was synthesized from the raw material VII-13 according to the synthetic method of compound 1. White solid, yield 61%. $^1$H NMR (400 MHz, DMSO) δ 7.60 (td, J=8.4, 1.6 Hz, 1H), 7.54-7.34 (m, 4H), 7.23 (t, J=74.0 Hz, 1H), 6.78-6.62 (m, 2H), 4.31 (s, 2H), 4.19 (s, 2H), 3.42 (s, 1H), 2.36-2.26 (m, 1H), 1.86-1.55 (m, 8H), 1.16-1.00 (m, 4H). MS(ESI, m/z): 569[M+H]$^+$.

Example 14

14

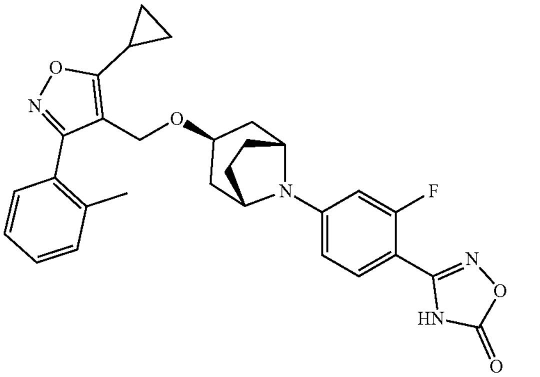

Example 14 was synthesized according to the following route.

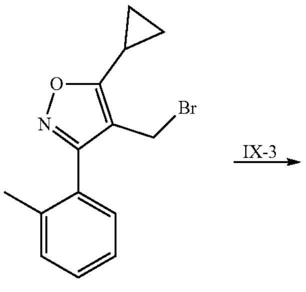

V-12

-continued

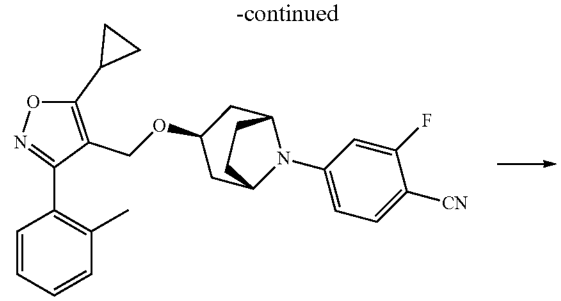

VII-14

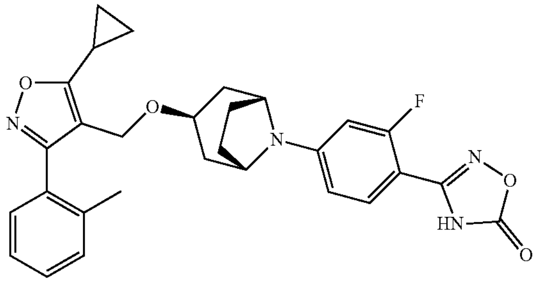

14

Compound intermediate VII-42 was synthesized from raw materials V-12 and IX-3 according to the synthetic method of compound VII-10. White solid, yield 49%. $^1$H NMR (400 MHz, $CDCl_3$) δ 7.39-7.24 (m, 5H), 6.46-6.41 (m, 1H), 6.39-6.34 (m, 1H), 4.21 (s, 2H), 4.13-4.06 (m, 2H), 3.50-3.43 (m, 1H), 2.31 (s, 3H), 2.15-1.87 (m, 7H), 1.75-1.67 (m, 2H), 1.29-1.09 (m, 4H).

Compound 40 was synthesized from the raw material VII-40 according to the synthetic method of compound 1. White solid, yield 61%. $^1$H NMR (400 MHz, $CDCl_3$) δ 7.66 (t, J=8.8 Hz, 1H), 7.37-7.22 (m, 4H), 6.52 (dd, J=9.0, 2.0 Hz, 1H), 6.39 (dd, J=14.9, 2.0 Hz, 1H), 4.20 (s, 2H), 4.09 (s, 2H), 3.49-3.43 (m, 1H), 2.31 (s, 3H), 2.17-1.89 (m, 7H), 1.69 (d, J=14.5 Hz, 2H), 1.28-1.08 (m, 4H). MS(ESI, m/z): 517[M+H]$^+$.

Examples of Pharmacological Experiments

Test Method for FXR Activity at the Molecular Level

FXR activity was determined using recombinant GST-FXR fusion protein by AlphaScreen detection reagent from PerkinElmer. The reaction in this method was carried out in a 384-well plate, and the total reaction volume was 15 μL. A mixture of protein, agonist, co-regulatory factor, AlphaScreen® acceptor beads and AlphaScreen® donor beads was reacted in a buffer containing Tris-HCl 50 mM (pH7.4), 50 mM NaCl, BSA 0.1%, and 1 mM DTT. The FXR activity was reflected by the fluorescence signal intensity at 570 nm wavelength detected by the Envision fluorescence detector. The value of $EC_{50}$ was calculated by the software Graphpad Prism 5 (A=EC50<10 nM; B=10 nM<EC50<100 nM; C=100 nM<EC50<1000 nM; D>1000 nM).

Test Method for FXR Activity at the Cellular Level

The FXR expression plasmid and FXRE luciferase reporter plasmid at a ratio of 1:9 were co-transfected into 293T cells, and then the transfected cells were seeded on a 96-well flat-bottom microplate (ViewPlate-96, White 96-well Microplate with Clear Bottom, PerkinElmer) at $5\times10^5$/well. The cells were cultured for 24 hours to ensure plasmid expression. Then the FXR receptor agonists to be tested were added and incubated for 18 hours. The fluorescence intensity was detected using a luciferase kit (steady-Glo Luciferase Assay system) to reflect the compound's activation efficiency on the FXR receptor.

OCA

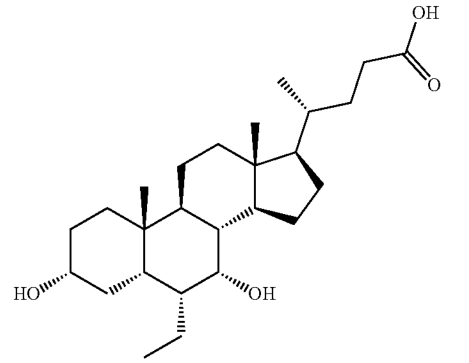

GW4064

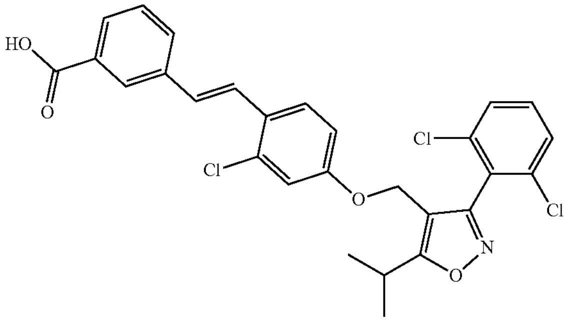

In the preliminary screening, the compounds to be tested and the two positive compounds OCA, GW4064 acted on the cells at 10 μM, and the relative activities of the tested compound to the two positive compounds were determined respectively (relative activity=(signal intensity of test compound−blank)/(signal intensity of positive compound−blank)×100%). The compound, the relative activity of which is higher than 50 of the positive compound entered the re-screening. The appropriate concentration interval was selected, and the dose-dependent relationship, that is, the $EC_{50}$ value (A=EC50<0.1 nM; B=0.1 nM<EC50<1 nM; C=1 nM<EC50<10 nM; D=10 nM<EC50<100 nM; E>100 nM), was calculated.

TABLE 1

Activity test results

| Tested sample | FXR activity at the molecular level $EC_{50}$ | FXR activity at the celluar level Activity relative to OCA (%) 10 μM | $EC_{50}$ |
|---|---|---|---|
| OCA | C | 100 | E |
| GW4064 | C | 106 | D |
| Example 1 | A | 88 | C |
| Example 2 | D | 73 | E |
| Example 3 | B | 116 | B |
| Example 4 | A | 103 | A |
| Example 5 | B | 141 | B |
| Example 6 | B | 122 | B |
| Example 7 | B | 117 | B |
| Example 8 | A | 102 | A |
| Example 9 | B | 102 | B |

TABLE 1-continued

Activity test results

| Tested sample | FXR activity at the molecular level $EC_{50}$ | FXR activity at the celluar level: Activity relative to OCA (%) 10 μM | FXR activity at the celluar level: $EC_{50}$ |
|---|---|---|---|
| Example 10 | B | 102 | B |
| Example 11 | B | 108 | C |
| Example 12 | B | 105 | C |
| Example 13 | B | 108 | B |
| Example 14 | B | 106 | B |

Conclusion: The test results show that the compounds of the present invention have good agonistic ability to FXR at the molecular level and the cellular level, the activities of endo-compounds are significantly better than those of exo-compounds, and the activity on FXR at the molecular level differs by at least 10 times. Compounds 1 and 2 are taken as examples, the activity of endo-compound 1 in Example 1 is much better than that of exo-compound 2 in Example 2 (the activity on FXR at molecular level differ by more than 100 times), and the activity of endo-compound is significantly better than those of the two positive controls.

All documents mentioned in the present invention are cited as references in this application, just as each document is individually cited as a reference. In addition, it should be understood that after reading the above teaching content of the present invention, those skilled in the art can make various changes or modifications to the present invention, and these equivalent forms also fall within the scope defined by the appended claims of the present application.

The invention claimed is:

1. A compound represented by general formula I, or a tautomer, or pharmaceutically acceptable salt thereof, (I)

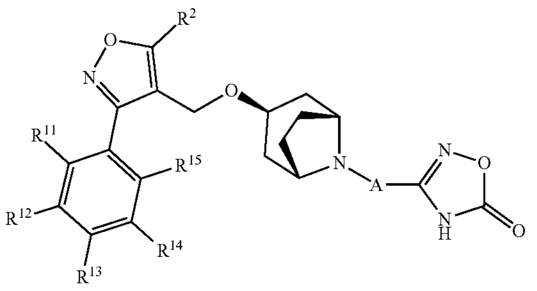

wherein $R^{11}$, $R^{12}$, $R^{13}$, $R^{14}$ and $R^{15}$ are each independently hydrogen, halogen, halogenated $C_{1-6}$ alkyl, halogenated $C_1$-$C_6$ alkoxy, $C_1$-$C_6$ alkyl, $C_{1-6}$ alkoxy, $C_3$-$C_6$ cycloalkyl, $C_3$-$C_6$ cycloalkoxy, cyano or nitro;

$R^2$ is $C_6$-$C_{12}$ aryl, $C_1$-$C_6$ alkyl or $C_3$-$C_6$ cycloalkyl;

A is the following substituted or unsubstituted group: phenyl, pyridyl, thienyl, furyl, indazolyl, indolyl, benzothienyl, benzofuranyl, and the "substituted" means that there is one, two or three substituents selected from the group consisting of halogen, $C_1$-$C_6$ alkyl, halogenated $C_{1-6}$ alkyl, halogenated $C_1$-$C_6$ alkoxy, $C_3$-$C_6$ cycloalkyl, $C_1$-$C_6$ alkoxy, and $C_3$-$C_6$ cycloalkoxy.

2. The compound of claim 1, wherein $R^{11}$, $R^{12}$, $R^{13}$, $R^{14}$ and $R^{15}$ are each independently hydrogen, fluorine, chlorine, bromine, methyl, ethyl, n-propyl, isopropyl, n-butyl, isobutyl, trifluoromethyl, or trifluoromethoxy.

3. The compound of claim 1, wherein $R^2$ is phenyl, methyl, ethyl, n-propyl, isopropyl, n-butyl, isobutyl, cyclopropyl, cyclobutyl or cyclopentyl.

4. The compound of claim 1, wherein A is the following substituted or unsubstituted group: phenyl, pyridyl, thienyl, furyl, indazolyl, indolyl, benzothienyl, benzofuranyl; and the "substituted" means that there is one or two substituents selected from the group consisting of fluorine, chlorine, bromine, $C_1$-$C_4$ alkyl, $C_3$-$C_6$ cycloalkyl, $C_1$-$C_4$ alkoxy, and $C_3$-$C_6$ cycloalkoxy.

5. The compound of claim 1, wherein A is phenyl,

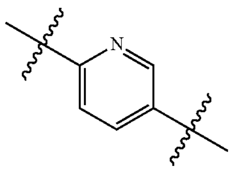

or

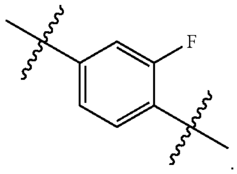

.

6. The compound of claim 1, wherein the compound is:

1

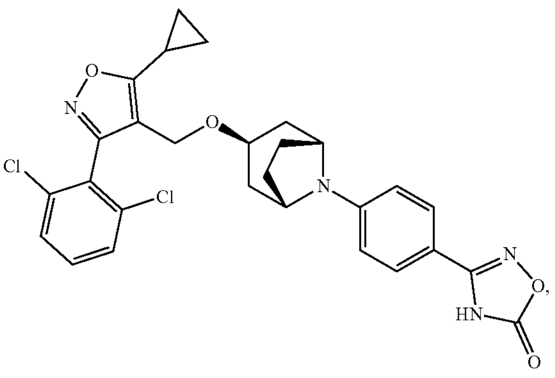

3

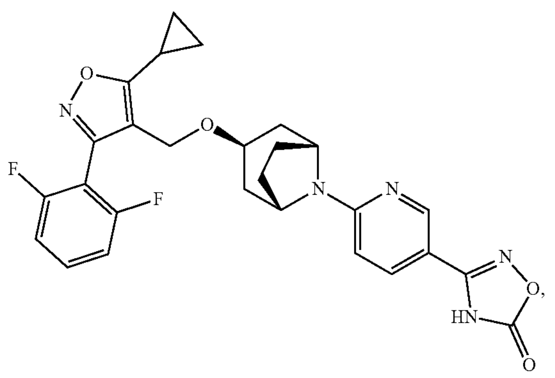

-continued
4
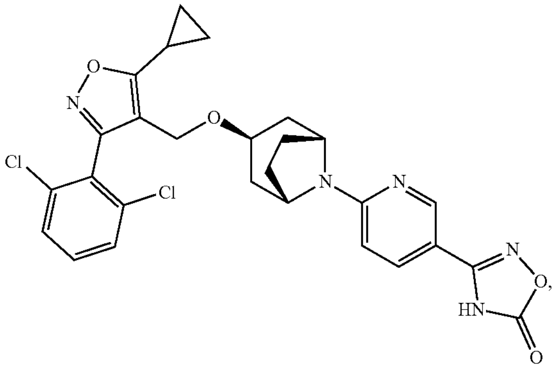
5
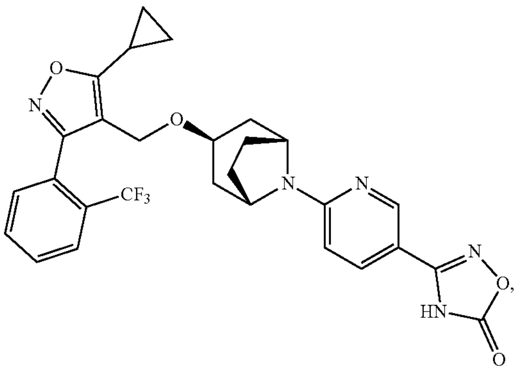
6
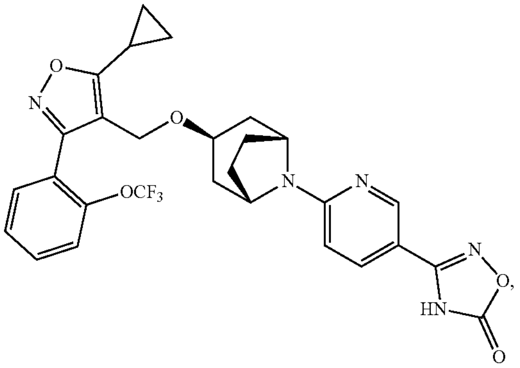
7
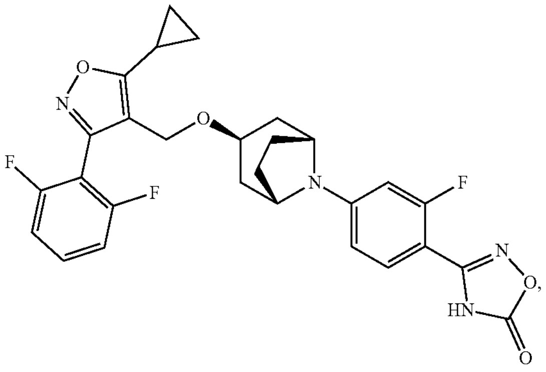
-continued
8
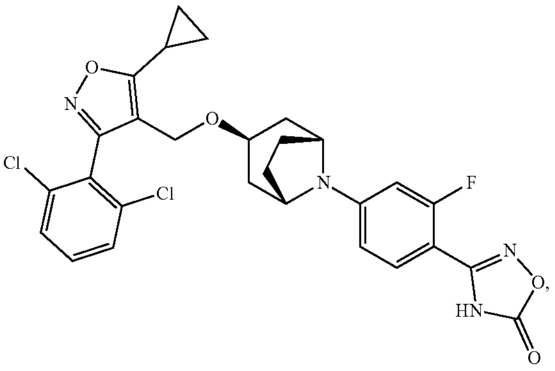
9
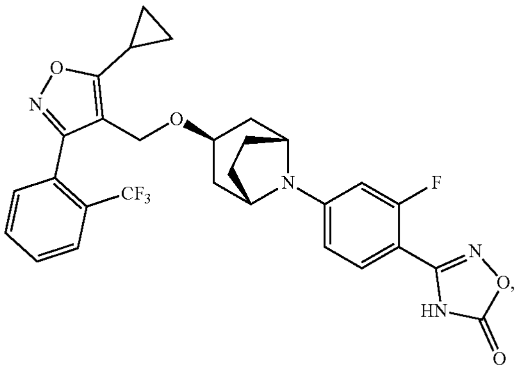
10
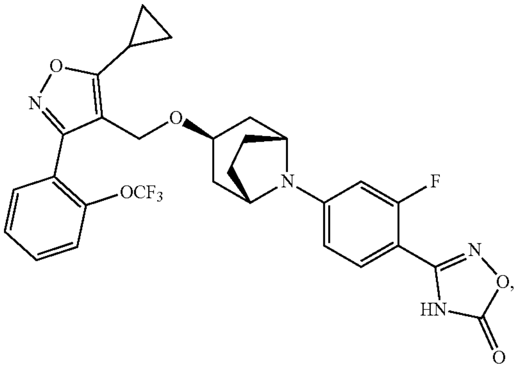
11
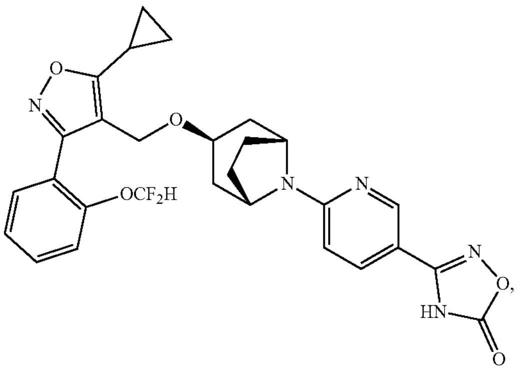

-continued

12

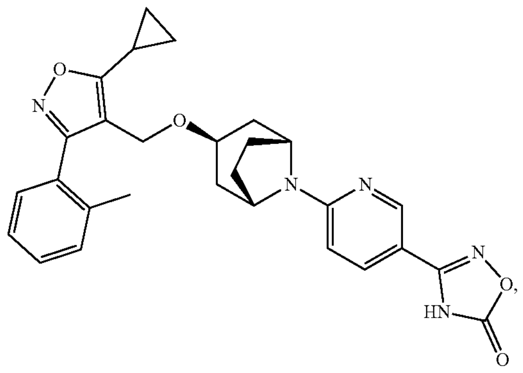

13

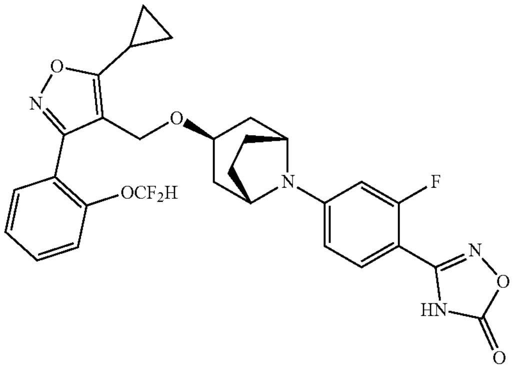

or

14

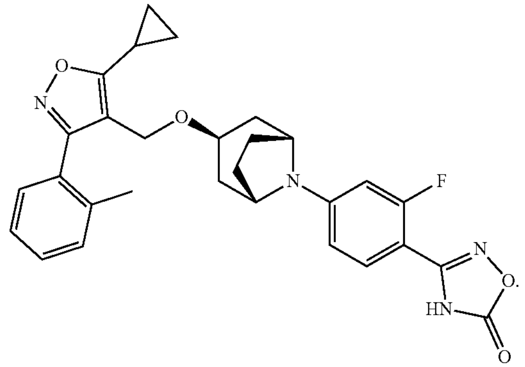

7. A method for preparing the compound according to claim 1, wherein the method comprises the following steps:

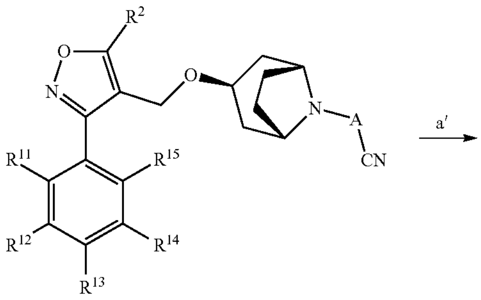

VII

-continued

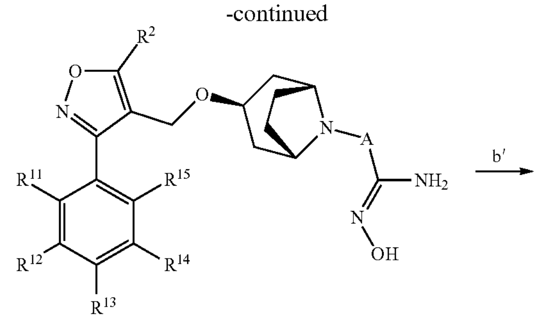

VIII

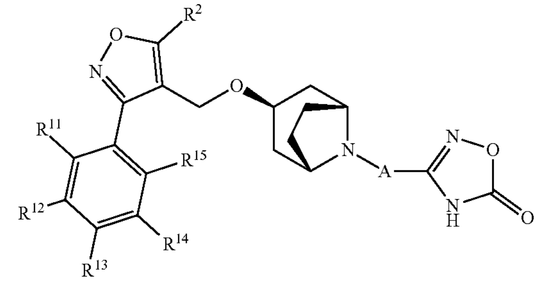

I (a') reacting a compound represented by general formula VII with hydroxylamine hydrochloride to produce a compound represented by general formula VIII;

(b') reacting the compound represented by the general formula VIII under the action of phosgene, triphosgene, carbonyl diimidazole or dimethyl carbonate to produce the compound represented by the general formula I, wherein $R^2$, A, $R^{11}$, $R^{12}$, $R^{13}$, $R^{14}$ and $R^{15}$ are defined as in claim 1.

8. The method of claim 7, wherein the compound represented by the general formula VII is prepared by the following steps:

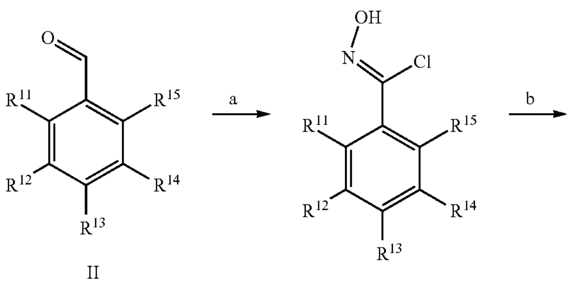

II

III

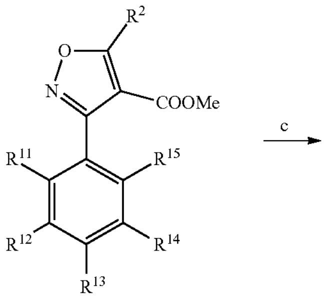

IV

-continued

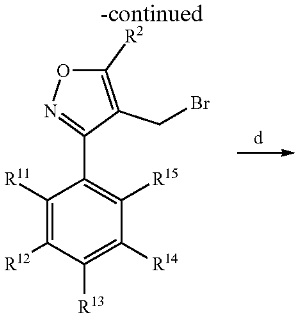

V

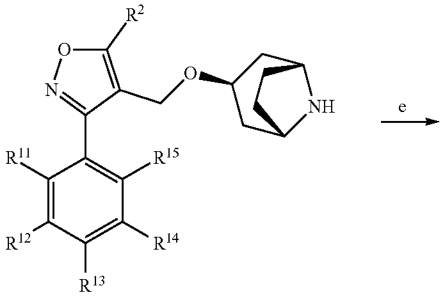

VI

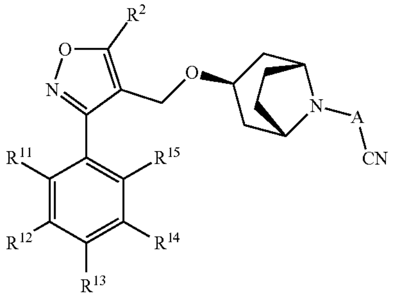

VII a) reacting substituted benzaldehyde compound represented by general formula II as starting materials with hydroxylamine hydrochloride to obtain an intermediate and then chlorinating the intermediate with N-chlorosuccinimide (NCS) to produce a compound represented by general formula III;

b) reacting the compound represented by the general formula III with 3-oxopropionate to obtain a compound represented by the general formula IV;

c) reducing the ester in the compound represented by formula IV to produce alcohol, and then brominating to produce a compound represented by V;

d) reacting the compound represented by general formula V with endo-8-azabicyclio [3.2.1] octan-3-ol to produce a compound represented by general formula VI;

e) coupling the compound represented by general formula VI with Br-A-CN under the catalysis of copper or palladium to obtain the compound represented by general formula VII, and, in each formula, $R^2$, A, $R^{11}$, $R^{12}$, $R^{13}$, $R^{14}$ and $R^{15}$ are defined as in claim 1, or the compound represented by general formula VII is prepared by the following steps:

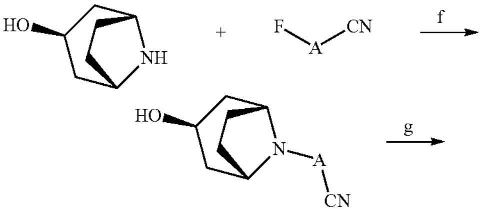

IX

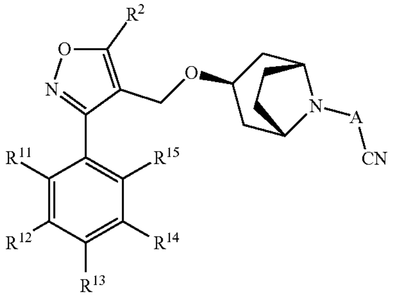

VII f) reacting endo-8-azabicyclio [3.2.1] octan-3-ol with F-A-CN to generate a compound represented by general formula IX;

g) reacting a compound represented by the general formula V with the compound represented by the general formula IX to produce the compound represented by the general formula VII, and, in each formula, $R^2$, A, $R^{11}$, $R^{12}$, $R^{13}$, $R^{14}$ and $R^{15}$ are defined as in claim 1.

9. A pharmaceutical composition comprising the compound represented by the general formula I of claim 1, or the tautomer, or pharmaceutically acceptable salt thereof; and a pharmaceutically acceptable carrier.

10. A method for treating an FXR-related disease comprising administering to a subject in need thereof the compound represented by the general formula I of claim 1, or the tautomer, or pharmaceutically acceptable salt thereof;

wherein the FXR-related disease is non-alcoholic fatty liver, primary biliary cirrhosis, primary sclerosing cholangitis, gallstone, non-alcoholic liver cirrhosis, liver fibrosis, cholestatic liver disease, hyperlipidemia, or diabetes.

11. The compound of claim 1, wherein $R^{12}$, $R^{13}$ and $R^{14}$ are hydrogen;

$R^{11}$ and $R^{15}$ are each independently hydrogen, chlorine, bromine, trifluoromethyl, or trifluoromethoxy.

12. The compound of claim 1, wherein A is a substituted or unsubstituted phenyl or pyridyl group; and the "substituted" means that there is one or two substituents selected from the group consisting of fluorine, chlorine, bromine, $C_1$-$C_4$ alkyl, $C_3$-$C_6$ cycloalkyl, $C_1$-$C_4$ alkoxy, and $C_3$-$C_6$ cycloalkoxy.

13. The compound of claim 1, wherein the pharmaceutically acceptable salt is a salt formed from an inorganic acid selected from the group consisting of phosphoric acid, sulfuric acid, and hydrochloric acid, or a salt of an organic acid selected from the group consisting of acetic acid, tartaric acid, citric acid, and malic acid; or a salt of an acidic amino acid selected from the group consisting of aspartic acid and glutamic acid; or a salt formed from an inorganic base selected from the group consisting of sodium, potassium, calcium, aluminum and ammonium salt.

* * * * *